United States Patent [19]
Hardy et al.

[11] Patent Number: 5,851,817
[45] Date of Patent: Dec. 22, 1998

[54] SPECIES SPECIFIC EGG-BINDING PROTEINS OF SPERM

[75] Inventors: Daniel M. Hardy, Dallas; David L. Garbers, Irving, both of Tex.

[73] Assignee: Board of Regents, The University of Texas System, Austin, Tex.

[21] Appl. No.: 276,967

[22] Filed: Jul. 19, 1994

[51] Int. Cl.$^6$ ............................................. C12N 15/12
[52] U.S. Cl. .................. 435/252.3; 536/23.5; 536/24.31; 536/24.33; 435/320.1; 530/350
[58] Field of Search ............................... 536/23.5, 24.31, 536/24.32, 24.33; 435/320.1, 252.3, 325, 419; 530/350

[56] References Cited

PUBLICATIONS

Young, et al., *PNAS*, vol. 80, Mar. 1983, pp. 1194–1198.
Bliel and Wassarman, "Identification of a ZP3–binding protein on acrosome–intact mouse sperm by photoaffinity crosslinking," *Proc. Natl. Acad. Sci. USA*, 87:5563–5567, 1990.
Cheng et al., "Sperm–Egg Recognition in the Mouse: Characterization of sp56, A Sperm Protein Having Specific Affinity for ZP3," *The Journal of Cell Biology*, 125(4):867–878, 1994.
Fernandez et al., "Internal Protein Sequence Analysis: Enzymatic Digestion for Less Than 10 μg of Protein Bound to Polyvinylidene Difluoride or Nitrocellulose Membranes$^1$," *Analytical Biochemistry*, 201:255–264, 1992.
Gao et al., "Sequence of mRNA coding for bindin, a species–specific sea urchin sperm protein required for fertilization," *Proc. Natl. Acad. Sci. USA*, 83:8634–8638, 1986.
Hardy and Garbers, "Molecular Basis of Signaling in Spermatoza," *Molecular Biology of the Male Reproductive System*, 233–270, 1993.
Hedrick and Hardy, "Isolation of Extracellular Matrix Structures from Xenopus laevis Oocytes, Eggs, and Embryos,m" *Methods in Cell Biology*, 36:231–247, 1991.
Hilkens et al., "Cell membrane–associated mucins and their ashesion–modulating property," *Trends Biochem. Sci.*, 17:359–363, 1992.
Jonakova et al., "Isolation and biochemical characterization f a zona pellucida–binding glycoprotein of boar spermatozoa," *FEBS Letters*, 280(1):183–186, 1991.
Kinloch et al., "Genomic Organization and Polypeptide Primary Structure of Zona Pellucida–Glycoprotein hZP3, the Hamster Sperm Receptor," *Developmental Biology*, 142:414–421, 1990.
Lathrop et al., "cDNA Cloning Reveals the Molecular Structure of A sperm Surface Protein, PH–20, Involved in Sperm–Egg Adhesion And the Wide Distribution of Its Gene among Mammals," *The Journal of Cell Biology*, 111(6) (Pt. 2):2939–2949, 1990.
Lopez et al., "Evidence for a Molecular Distinction between Golgi and Cell Surface Forms of β1,4–Galactosyltransferase," *The Journal of Biological Chemistry*, 266(24):15984–15991, 1991.
Macek et al., "Aggregation of β–1,4–Galactosyltransferase on Mouse Sperm Induces the Acrosome Reaction," *Developmental Biology*, 147:440–444, 1991.
Mayadas and Wagner, "Vicinal cysteines in the prosequence play a role in von Willebrand factor multimer assembly," *Proc. Natl. Acad. Sci. USA*, 89:3531–3535, 1992.
Miller et al., "Complementarity between sperm surface β–1,4–galactosyl–transferase and egg–coat ZP3 mediates sperm–egg binding," *Nature*, 357:589–593, 1992.
Minor et al., "Species–Specific Inhibition of Fertilization by a Peptide Derived from the Sperm Protein Bindin," *Molecular Biology of the Cell*, 4:375–387, 1993.
Minor et al., "Comparison of the Bindin Proteins of *Strongylocentrotus franciscanus*, *S. purpuratus* and *Lytechinus variegatus*: Sequence involved in the Species Specificity of Fertilization," *Mol. Biol. Evol.*, 8(6):781–795, 1991.
Moller et al., "Structural and Functional Relationships between Mouse and Hamster Zona Pellucida Glycoproteins," *Developmental Biology*, 137:276–286, 1990.
O'Rand et al., "Identification of Zona Binding Proteins of Rabbit, Pig, Human, and Mouse Spermatozoa on Nitrocellulose Blots," *The Journal of Experimental Zoology*, 235:423–428, 1985.
Parry et al., "Characterization of Low Mr Zona Pellucida Binding Proteins From Boar Spermatozoa and Seminal Plasma," *Molecular Reproduction and Development*, 33:108–115, 1992.
Peterson et al., "Interaction of Boar Spermatozoa With Porcine Oocytes: Increase in Proteins with High Affinity for the Zona Pellucida During Epididymal Transis," *Gamete Research*, 14:57–64, 1986.
Primakoff et al., "Identification and Purification of a Sperm Surface Protein with a Potential Role in Sperm–Egg Membrane Fusion," *The Journal of Cell Biology*, 104:141–149, 1987.
Sacco et al., "Porcine Zona Pellucida: Association of Sperm Receptor Activity with the α–Glycoprotein Component of the $M_r$=55,000 Family," *Biology of Reproduction*, 41:523–532, 1989.
Shur, "Expression and function of cell surface galactosyltransferase," *Biochimica et Biophysica Acta.*, 988:398–409, 1989.

(List continued on next page.)

*Primary Examiner*—Keith D. Hendricks
*Attorney, Agent, or Firm*—Arnold, White & Durkee

[57] ABSTRACT

Disclosed are compositions which bind to mammalian egg zona pellucida in species-specific fashion. Also disclosed are methods for speciating mammalian eggs, identifying species-specific sperm, and providing contraception in a mammalian population. Specifically disclosed are nucleic acid sequences and the corresponding amino acid sequences of specific sperm membrane proteins they encode, whose identification and characterization have permitted development of species-specific contraceptive and fertility compositions and methods.

19 Claims, 24 Drawing Sheets

OTHER PUBLICATIONS

Urch and Patel, "The interaction of boar sperm proacrosin with its natural substrate, the zona pellucida and with polysulfated polysaccharides," *Development*, 111:1165–1172, 1991.

Vassar et al., "Spatial Segregation of Odorant Receptor Expression in the Mammalian Olfactory Epithelium," *Cell*, 74:309–318, 1993.

Ward and Kopf, "Molecular Events Mediating Sperm Activation," *Developmental Biology*, 158:9–34, 1993.

Wassarman, "Zona Pellucida Glycoproteins," *Ann. Rev. Biochem.*, 57:415–42, 1988.

Wassarman, "Mouse Gamete Adhesion Molecule," *Biology of Reproduction*, 46:186–191, 1992.

Williams and Jones, "Specificity of Binding of Zona Pellucida Glycoproteins to Sperm Proacrosin and Related Proteins," *The Journal of Experimental Zoology*, 266:65–73, 1993.

Yurewicz et al., "Nucleotide sequence of cDNA encoding ZP3α, a sperm–binding glycoprotein from zona pellucida of pig oocyte," *Biochmica et Biophysica Acta*, 1174:211–214, 1993.

```
          10        20         30         40         50         60         70
GGTGGCGGGTGTAAGGAGGTGCCTGCCCTTCAGCTTCAGGCCCGCACTCTCAGGGATTTGTGTGAATCAT          70
CTCTGTACAGTGGGTCGAGAAAAGGAAGAGGATGTGGCTCTAGGGACTTCAAAAGCCACCATTTGAAGG         140
ACAAGATTCTGGCCTGTGCTTCTGAGAGGATGCCGCGGATTCCTAGGCAGCGCCCCCACCCTCACCCAGAC       210
CTGCCAAACGCGCTTCTGGAAGGATCCGAGGCCTCAGCTCGCGTGGCCGGGTGTAGGCCACCTCGGTGC         280
TGGCTGATCCTAGGGAGATGTTAGGGCTCCCTGCCCTCGCAGGCCCTATGGCTATGCCACACCCACCTCT        350

360       370        380        390        400        410        420
AATTCCCCTCCACTCCCACTTTATTGGCCTTTCCTTCCCAGGTGGCTTCTACATGCTCCTGGACCCCAAG        420
AATGCAAAACCAAGGCAAAGATCTGCCCTCCTGAGCCCTCTGATCCAGTCCTCCGGCTGCCTGAGCCTGT        490
CCTTTCAGTACACCCAAGTGGCCAGGGTCTGGTGCAACCCTCATGGTCTATGCTTCTGTTTTGGGCAG         560
CATCCGGAAACACACTCTTTTCTCAGGACAACCCGAGTTGGCAGCCTGTTTCTGTCAATTACACA            630
AGCCAAGGACAGATTCAGTTCACCCTGGGTGTGTTTGGAAAAGATCCCAGAGCCAGCTGTGGCAGTAG         700

710       720        730        740        750        760        770
ATGCAATCAGCATTGCTCCCTGTGAAGAGAGCTTTCCTCAGTGTGACTTTGAAGATAATGCCCATCCCTT       770
CTGTGACTGGGTACAGGCATCACAGGATGGTGGAGgCAGGGAAATAAAAATACATTCATCCAG            840
CCTGCAGGCCCCTTTGGAATCTCCCTTAATGGAGAAGGTCACTACATCTTCCTTGAGACTGACAAGTTCT       910
CCCAGGCAGGCCAGTCTTTCAGACTGGGTGAGCCGGCCCTTCTGTGCCCGGCTGTGATCTGCGTGACGTT       980
TACCTACCACATGTATGGGACAGGGCACAAAGCTCAGGCTGCTGCTGGGGAGTCCTGCGGGTAGT           1050
```

FIG. 7A

```
            1060      1070      1080      1090      1100      1110      1120
CCCCAAGTTCTCTGGGAAGTGTTGGGCCTCAGAGCCCTGAATGGCTGAACACCTCGTCACCATCC         1120
CTTCAGGACATCAACAGCCATGCAGCTGATATTTGAAGCGTCAGGGGCACCAACACCGCCTTTGTT       1190
TGCTCTGGGTTTCGTCTTGATCAATCATGGGACCTGTGAGGACCTTCTGAAACCTCTGTCTCCACAGAA    1260
AAACCGTGGCCCCTACAGAAAAACCAACTGTCCCAGTGAAATATACACTATCCCCACAGAAAAGCCCA     1330
TGGTCCACATGGAGAAGCCCATTGTACACACTGAAAAACCTACAGTTCCCACAGAAAACCTACAATCCC    1400

1410      1420      1430      1440      1450      1460      1470
AACAGAAAAATCTACAGTGCCCACCAAAAAACCCACTGTCTTTAAAGAACCCACCCTTCCACCTGAAGGG   1470
CCCACCGTCCCTGTGAACGGCTACCACCCGCCTGAAGGGCCTGCTGCCCTCCTAAAGGGCCCACTG       1540
TCCTCACTGAATGGCCACAAGCCACAGCCACAGAGAAAATCTACTGTCCACACAGAGAAACCATTCTCCCAC 1610
AGGAAAATCCACCATCCCCACAGAAAAACCCATGGTCCCCACCAAAAGGACCACCACTCCCACTGAAAGG   1680
ACCACTATCCCCGCAGAAAAGCCAACTGTCCCCATAGAAAAACCAATGGTCCCCACGGAAAGGACCACCA   1750

1760      1770      1780      1790      1800      1810      1820
TTCCCACTGAAAAGAACCACCACTATCCCCACAGAAAAACCTACTGTTCCCACAGAAAACTCACTGTCCCCAC   1820
AGAAAAGCCAATTGTCCCCACAGaAAAAGCCGATTGTCCCCACAGAAAAACACCATCCCCACAGaAAAA     1890
CTGACAGTCCTCACTGAGAGGACCACTACTGTCCCACAGAAGAACCACTATCCCCACAGAAAACCTACTG    1960
TCCCCACAGaAAAACCCTCTGTCCCACAGAAAAGCCAACTGTCCCCACAGAAGAACCACCATCCCCAC     2030
AGAAAAGCTTACGTCCCCACTGAGAGGACCACTCCCAAAGGaCCACCACTCCCACCATAAGG           2100
```

FIG. 7B

```
         2110       2120       2130       2140       2150       2160       2170
aCCACCACCCCCACCATAAGGACCACCCCCACCGAAAGGACCACCCCCACCATAAGGACCACCA   2170
CTCCCACTGAAAGGACCACCATCCCCACGAAAAAGACCACTGTTCCCACAGAAAAAACCATTATCCCCAC   2240
TGAAAGGACCATAGCTCCTACAACACCCCAGcCCAGCCCAACTCTTGTACCCACTCAGCCAGCAGCCGTC   2310
GTGATGCCAAGTACTTCCGGACCACTGTGACCCCGAGAACTACTATAGGGAGCTGCCCCCAAATGCCC   2380
ACTTTGAACGCTGCGCCTGCCCCAGTGTCCTGCCAGAGCCCCACACCCCAACTGTGAGCTCTTCTGCAAGCC   2450

2460       2470       2480       2490       2500       2510       2520
CGGCTGTGTCTGTGATCCTGGCTTTTTATTCAGTGGCTCCCACTGCGTCAACGCCTCTTCCTGTGATTGC   2520
TTCTACAACGACAATTACTATAAGCTGGGGACAGATTGGTTCAGCCCAACTGCACAGAACATTGCCACT   2590
GCCGGCCCAGCAGTCGGATGGAGTGCCAGACCTTCAAGTGCGGGACACACAGTGTGCCAGCTGAAGAA   2660
TGGCCAGTACGGCTGCCACCCTATGCCAGTGCCACCTGTCTGTTACGGAGACCCTCACTACCTCACC   2730
TTCGACGGGAGGCGCTTTAACTTCATGGGCAAGTGCACCTACATCTTGGCCCAACCCTGTGGCAACTTGA   2800

2810       2820       2830       2840       2850       2860       2870
CAGAGCACTTCTTCAGGGTGCTGGTGAAGAAGGAGGAGCAGGAGGGCGTGTCCTGCCTAAGCAA   2870
GGTCTACGTGACTCTGCCTGAAAGCACGTCACTCTGCTCAAGGGCAGACACACGCTGGTCGGAGGTCAG   2940
CGAGTCACCCTCCCAGCCATACCTTCTAGAGGTGTCTTCCTGGCTCCCAGTGGGCGATTTGTGGAGCTGC   3010
AGACGGCGTTCGGTCGCGGGTGAGATGGTGACCAGCAGTGTTTGTGAGTGTGCCAGCACCTT   3080
CTCTGGCAAACTCTGTGGTCTCTGTGGCGACTATGACGGTGACAGCAGCAACGAGAAGCCGGAT   3150
```

FIG. 7C

```
       3160       3170       3180       3190       3200       3210       3220
GGCAGTCCAGCAAAAGATGAGAAGGAGCTGGGTAGCAGCTGGCAGACCTCGGAGGATGCGGACCAGCAGT          3220
GCGAGGAGAACCAGGTGTCTCCCCGTCTTGCAACACGGCCTTGCAGAaTACTATGTCGGGGCCAGAGTT          3290
CTGTGGACAGCTGGTGGCCCTCATGGAGTCTTCGAGGGTGCCTGCTGCCTCACCTCAGGGCCTCCTTC          3360
TTCAAGAGCTGCACGTTTGACATGTGTAACTTCCAGGGCTGCAGcATATgCTGTGTGCTCACATGTCGG          3430
CCTTGACTGAGAACTGCCAGGATGCTGGCTACACGGGTGAAGCCCTGGAGAGAGACCCCAGTTCTGCCCGCT       3500

3510       3520       3530       3540       3550       3560       3570
GGCCTGCCCCGCAACAGTAGGTACACGCTGTGTGCCAgGCTGTGCCCCGACACCTGCCATTCTGAGTTC          3570
TCGGGCAGGGCTGCAAGGACCGCTGCGTGGAGGGCTGCGAGTGCGACCCAGGCTTCGTCCTCAGTGGCC          3640
TCCAGTGCGTCTCCCGGTCTGCCTGCTCCGAGTGTGGCTGCCTCGACTCCACAGCGGGTTATGTCAAGGTAGGGAGCG 3710
GTGGTTCAAGCCAGGCTGCAGACAGCTCTGTATCTGTGAGGGTAACAACAGAACTCGCTGTGTGCTCTGG         3780
AGGTGCCAGGCCCAGGAGTTCTGCGGGTCAGCAGGATGGCATCTACGGCTGCCATGCTGCCAAGGGTCTGCCA      3850

3860       3870       3880       3890       3900       3910       3920
CCTGCACTGTCTCGGGGGACCCCCACTACCTGACGTTCGACGGAGCCCTGCACCACTTCACGGGCACCTG         3920
CACCTACACCCTGACCAAACCCTTGCTGActGAGGTCCCTAGAGAATTCTTTCCTTGTGAGTGCCACCAAT        3990
GAGTTCCGCGGTGGAAATTTAGAGGCCTCCACGTCCTACGTCAGAGAGCCGTCCAGGTGCAGGTCTTCAACCTCAGAA 4060
TCTCGCTGATCAAAGCCGCAAAGTCACGCTGGATGCCGCCAGGGTGGCCTTGCCCTGTGCCGCACA             4130
AGGCCGGGTGAGCATCACGTCCAGTGGCTCCTTCATCCTCCTCTACACGGACTTTGGGCTTCAAGTTCGC         4200
```

FIG. 7D

```
              4210      4220      4230      4240      4250      4260      4270
TATGATGGCGACCACCTGGTGGAAGTGACCGTGCCCTCCTCCTACGTGGCCTGGCCGGCTCTCTGTGGGCTCTGCG   4270
GGAACTACAACAACAGCCTGGACGACATTCTGCAGCCTGATAAAAGGCCTGCAAGCAGCTCTGTGCG           4340
CCTGGGGCCTCCTGGAAGATAAATGAGTTATCTGAACCTGGCTGCTTTGCTGAAGGTGCAAGCCCCC           4410
AGGTGCCTGGGGAAGGAAGTGGCAGAGCGCCTGGCGTAAGAACTGTGATGTCTTAATGAACCCTCAGGGAC       4480
CCTTCTCTCAATGCCACAGGGTGGTGGCCCCTCAATCCAGCTTCTCCAGCTGTTTGTATGGCCAGTGTGC        4550

4560      4570      4580      4590      4600      4610      4620
GACCAAGGGGGACACCCTGACCCTGTGCCGCTCCCTGCAGGCCTACGCGTCCCTGTGCGCGCGCTGGC          4620
CAGGCCCTCACCTGGCGGAATGGCACCTTCTGCCCTCTGAAGTGCCGTCAGGCAGCAGCTATAGCACCT         4690
GTGCCAACCCCCTGCCCAGCCACCTGCCTCAGCCTCAGCCCATCATATGCCATCCACGCTGCCCTG            4760
TGCCGAGGGCTGCGAGTGCCAGAAAGGCCACATCTTGAGGCGAACCTCCTGcGTGCCCCTCAGCCAGTGT        4830
GGCTGcACCACCCAGAGAGGGCTCCTACCACCCGGTTGGGGAGAGCTGGTACACGGACAACAGCTGCTCCA       4900

4910      4920      4930      4940      4950      4960      4970
GGCTCTGCACCTGCTCTGCCCACAACAACATCTCCTGCCGCCAGGCCTCCTGCAAGCCCAGCCAGATGTG        4970
CTGGCCCCAGGATGGGCTGATACGGTGCCGGGTGGCAGGGATGGGCAGGGATGTGCCGCATCCTGACACATCC     5040
CACTACGTGAGCTTCGATGGCAGCTACCATGCTGTCAGGGGCAACTGCACTTACGTCCTGGTGAAAATAT        5110
GCCACTCCaCCATGGACCTGCTTTCTTCAAGATCAGTGGCGAGAATGGGAAGCGGGAAGGCCAACCCCC         5180
GGCTTTCTACCTCCGCCAGGTCTACGTGGATATCTTTAATACCCTGGTCACCCTGAAACAGGACCAAGTG        5250
```

FIG. 7E

```
         5260       5270       5280       5290       5300       5310       5320
CTGATCAATGGCACACGGGTCAGTCTGCCTGCAACCACGCAGATCCGTGGGTCAGAGTCATTTCCAGGG   5320
ACGGCTACACCGTGCTCACCATCAACATCGGGGTGCAGGTCAAGTTTGACGGCAGAGGTTTCCTTGAGGT  5390
TGAAATCCCCAAAGCCTATTACGGAAGGACCTGCGGCGTGTGCGGGAACTTCAACGACGAGGAAGAAGAC  5460
GAGCTCATGATGCCCAGTGATGCACTAGCTCTGGATGACGTCATGTATGTGGACAGCTGGCGAGATAAGG  5530
AGATCGACCCAAATTGCCAGGAAGATGACAGGAAGACCGAAGCAGAATCGCAAGAGCAGCCAAGTGCAAA  5600

5610       5620       5630       5640       5650       5660       5670
CTGCAGGCCAGCTGACCTGGAGCGGAGCCAGGAGCCCAGGAGCAGTGCCAGGCGGCCTTTCAGGCCCCGGCCTGGGCA  5670
AACTGTGCCACCCGCGTGGTGCTCAGTCCCTACGTGCGCAGCTGTACTCACAAGCTCTGTGAGTTTGGAG  5740
GCCTAAAACGTGCCTTTGCGAGTCTCTGCAAGCCTTCGGGGCCGCCTGCCAGGCCCACAGCCCAGGGATCAAGCC  5810
CCCAGTCTGGAGAAACAGCAGCTTCTGCCCTCTGGACTGC[CCGCCCACAGCGTCTACACCTCCTGCGTC  5880
CCCTCCTGCCCTCCCTTCCTGCCAGGACCCCAGTGCACAGGCGCCGAAGCTCCCTCCACCTGTG          5950

5960       5970       5980       5990       6000       6010       6020
AGGAGGGCTGCATTTGTGAGCCCGGCTACGTGCTCAGCGAGCAGCAGTGTGGCCAGGAGTCAGTGCGG    6020
CTGCAGGGACGCCAGGGGCACTTTCCTTCCGTGGTAGGTTCCGGCTCCCAGGTTCCGGCTGCCTCCCAGATG  6090
TGTGTCTGCACAGCAGGGAGCCATTGAGTGAGAGCCCTTCACCTGCCCTCCGGCTCCCAGTGCGAGCCCA  6160
ACGAAGACGGCAAGGACTTCTGCCAACCCAACAGCTCCAATCTATGCTCAGTTTCGGGATCCCATTA     6230
CCGCACATTTGATGGCCTCAGCTACCGCTTCCAGGGCCGCATGACCTACACCCTGGTCAAGACCTTGGAC 6300
```

FIG. 7F

```
           6310      6320      6330      6340      6350      6360      6370
GTGCTCCCCGATgGGGTGGAGCCCCTGGTGGTGGAGGGACGCAACAAGGTGTATCCATCCTTAACCCGG      6370
TCTTCCTGCAAGAGATCATCGTCATGGTCTACGGCTACACAGTCCAGCTCCAGGCCGAACTGGAGCTTgt    6440
GGTCAACGGTCAGAAGGTGTCCATCCCCTACAAGCCCAAGCGAGTACCTGCAGGTCACTCTGCGAGGCGT    6510
CGCCTGTATCTGGTCACAGACTTTGAGCTGGTCGTCAGCTTCAATGGAAGAAACAATGCAGTGATCGCCA    6580
TGCCCAGCACCTACCTGGGGCTCGTGCGAGGCCTGTGCGGCAACTACGACAAGAACAAGAGAATGACTT    6650

6660      6670      6680      6690      6700      6710      6720
CATGCTGCCTAATGGCTCCTCTTCACCCAGAACCTCCTTGTCTTTGGCAACAGCTGGGAGGTAAAGGCCAAG  6720
GAAGGCCACCCCCGCTTCTCAAGGCCATTCGAGAGGAAGAGAAAAACGAAGAGTCAGGCTTTCAGA        6790
ATGTGTCAGAATGCAGCCCAGAGCTGGACTCGTCGTCAACCACCAGGCGTGTGGGGTGCTGGTGGA        6860
CCCTCAGGGCCCCtTTGCTGCCTGTCACCAGATTGTggCCCCAGGGCCCTTCCAGGAGCACTGTGTGTTT   6930
GATCTCTGTGCCCCGGCCTGCCCCAAAGAGCAGGAGAGTTGCGTTGCCAGGTCCTCAGCGGGTACGCCA    7000

7010      7020      7030      7040      7050      7060      7070
TCATCTGCCAGGAGTCGGAGgcCCCACCCTGGCCGGGACTGGGCGGGACCACACCCACTGGCCTTGCCATGTCC  7070
GGCCAACACGGTCTATCAGAGCTGTATGACACCCTGCCCAGCCTCCTGTGCCACCCTGGCACCCTGGCAGTCCCCGG  7140
gCCTGCGACGGCCCGTGTGTGGAGAggCTGTGCCAGCCTCCCCGGCCCTCCCGGTTACATCTACAGTGTGCCCAGAGCC  7210
TTCCCATGGCCCACTGTGGCTGCACCAACAACGGGTCTACTACCAGCAGGGTGACAGCTTCGTGACCGA       7280
GAACTGCTCTCAGCGCTGCACCTGTGCCAGCTGCACCTCGGGGTCCTGCTGTGTGAGCCCCTCAgCTGCCGCCCT   7350

FIG. 7G
```

```
      7360      7370      7380      7390      7400      7410      7420
GGGGAGATCTGCACCCTGGGGAACCTCACTCGTGGCTTCCGAGACAGCCCATGTCTACAGAACCCCT    7420
GTCAGAATGATgGGCGGTGTCGGGAGCAGGGAACCCACTTCACCTGTGAGTGTGAA/TTGGTTACGGGGG 7490
AGACCTCTGCACGGAGCCTCGGGGTGTACCATCCCCCAAAAAGCAGAGGGTCCAACCGTGGCCATC    7560
CTCTTGGGGATGCTGATGCCACAGTGCTCCTGGTGCCGGGTGACCAGAGTTTCCAGGAAGAGGAGGA   7630
GGAGGAGGCCCTCTAGGGAGAGAACGCAGAGCCAGAACAGAGGCAAGCGGGCGGCACAGATTGTGC    7700
      7710      7720      7730      7740      7750      7760      7770
TCCAGAGCAGGCCTACAAAGTGGCTTAGTTTTGAGGTGTTCACACAAAGGGAGAGATAAAATTATTTATT 7770
TTTGAAAAAAAAAA    7785
```

FIG. 7H

```
         10         20         30         40         50         60         70
MLGLPALAGPMAMPHPPLIPSTPTLLAFSFPGGFYMLLDPKNAKPRQRSALLSPLIQSSGCLSLSLSFQYTQ     70
RGQASGATLMVYASVLGSIRKHTLFSGQPGPSWQPVSVNYTSQGQIQFTLVGVFGKIPEPAVAVDAISIA      140
PCEESFPQCDFEDNAHPFCDWVQASQDGGYWRQGNKNTFIQPAGPFGISLNGEGHYIFLETDKFSQAGQS      210
FRLVSRPFCAPAVICVTFTYHMYGLGQGTKLRLLLGSPAGSPPSSLWERVGPQSPEWLNTSVTIPSGHQQ      280
PMQLIFEAVRGTNTAFVVALGFVLINHGTCRGPSETSVSTEKPVAPTEKPTVPSEIYTIPTEKPMVHMEK     350
PIVHTEKPTVPTEKPTIPTEKSTVPTKKPTVFKEPTLPPEGPTVPAERPTTPPEGPAVPPKGPTVLTEWP     420
TSHTEKSTVHTEKPILPTGKSTIPTEKPMVPTKRTTPTTPAEKPTVPIEKPMVPTERTTIPTERT          490
TIPTEKPTVPTEKLTVPTEKPIVPTEKPIVPTEKHTIPTEKLTVLTERTTIPTTIPTIRTTIPTERTTIPTIRTTIPTERT      560
SVPTEKPTVPTEEPTIPTEKTIIPTERTIAPTPQPSPTLVPTOPAAVVMPSTSATTVTPRTTIASCPPNAHFERCA      630
TIPTKKTTVPTEKTIIPTERTIAPTPQPSPTLVPTOPAAVVMPSTSATTVTPRTTIASCPPNAHFERCA      700
CPVSCQSPTPNCELFCKPGCVCDPGFLFSGSHCVNASSCDCFYNDNYYKLGTDWFSPNCTEHCHCRPSSR     770
MECQTFKCGTHTVCQLKNGQYGCHPYGSATCSVYGDPHYLTFDGRRFNFMGKCTYILAQPCGNLTEHFFR     840
VLVKKEERGQEGVSCLSKVYVTLPESTVTLLKGRHTLVGGQRVTLPAIPSRGVFLAPSGRFVELOTAFGL     910
RVRWDGDQQLFVSVPSTFSGKLCGLCGDYDGDSSNDNQKPDGSPAKDEKELGSSWQTSEDADQQCEENQV     980
SPPSCNTALQNTMSGPEFCGQLVAPHGVFEACLPHLRASSFFKSCTFDMCNFQGLQHMLCAHMSALTENC    1050
QDAGYTVKPWRGPQFCPLACPRNSRYTLCARLCPDTCHSEFSGRACKDRCVEGCECDPGFVLSGLQCVSR    1120
SECGCLDSTAGYVKVGERWFKPGCRQLCICEGNNRTRCVLWRCQAQEFCGQQDGIYGCHAQGSATCTVSG    1190
DPHYLTFDGALHHFTGTCTYTLTKPCWLRSLENSFLVSATNEFRGGNLEASYVRAVQVFNLRISLIKG     1260
RKVTLDGRRVALPLWPAQGRVSITSSGSFILLYTDFGLQVRYDGDHLVEVTVPSSYAGRLCGLCGNYNNN    1330
SLDDILQPDKRPASSSVRLGASWKINELSEPGCFAEGGKPPRCLGKEVADAWRKNCDVLMNPQGPFSQCH    1400
```

FIG. 8A

```
                10        20        30        40        50        60        70
RVVAPQSSFSSCLYGQCATKGDTLTLCRSLQAYASLCARAGQALTWRNGTFCPLKCPSGSSYSTCANPCP    1470
ATCLSLNNPSYCPSTLPCAEGCECQKGHILSGTSCVPLSQGCTTQRGSYHPVGESWYTDNSCSRLCTCS    1540
AHNNISCRQASCKPSQMCWPQDGLIRCRVAGMGVCRIPDTSHYVSFDGSYHAVRGNCTYVLVKICHSTMD   1610
LPFFKISGENGKREGQPPAFYLRQVYVDIFNTLVTLKQDQVLINGTRVSLPATTQIRGVRVISRDGYTVL   1680
TINIGVQVKFDGRGFLEVEIPKAYYGRTCGVCGNFNDEEEDELMMPSDALALDDVMYVDSWRDKEIDPNC   1750
QEDDRKTEAESQEQPSANCRPADLERAQEQCQAAFQAPAWANCATRVVLSPYVRSCTHKLCEFGGLNRAF  1820
CESLQAFGAACQAQGIKPPVWRNSSFCPLDCSAHSVYTSCVPSCLPSCQDPEGQCTGAGAPSTCEEGCIC  1890
EPGYVLSEQQCVARSQCGCRDARGTFLPVGRFRLSSGCSQMCVCTAGAIECRPFTCPSGSQCEPNEDGKD  1960
FCQPNSSNLCSVFGDPHYRTFDGLSYRFQGRMTYTLVKTLDVLPDGVEPLVEGRNKVYPSLTPVFLQEI   2030
IVMVYGYTVQLQAELELVVNGQKVSIPYKPNEYLQVTLRGRRLYLVTDFELVVSFNGRNNAVIAMPSTYL  2100
GLVRGLCGNYDKNKRNDFMLPNGSFTQNLLVFGNSWEVKAKEGHPRFSRAIREEEKNEESGFQNVSECS   2170
PEQLELVNHTQACGVLVDPQGPFAACHQIVAPGPFQEHCVFDLCAAPGPKEQEELRCQVLSGYAIICQES  2240
GPTLAGWRDHTHCALPCPANTVYQSCMTPCPASCATLAVPRACDGPCVEGCASLPGYIYSGAQSLPMAHC  2310
GCTNNGVYYQQGDSFVTENCSQRCTCASSGVLLCEPLSCRPGEICTLGNLTRGCFRDSPCLQNPCQNDGR  2380
CREQGTHFTCECELGYGGDLCTEPRGVPSPKKPEASNRVAILLGMLMPTVLLVPAVTRVSRKRRRRRPS   2450
RERTQSQNRGKRAGTDCAPEQAYKVAM   2477
```

FIG. 8B

SEQUENCE LISTING ( 1 ) GENERAL INFORMATION:

( i i i ) NUMBER OF SEQUENCES: 8

( 2 ) INFORMATION FOR SEQ ID NO:1:

( i ) SEQUENCE CHARACTERISTICS:
        ( A ) LENGTH: 7785 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:1:

```
GGTGGCGGGT  GTAAGGAGGT  GCCTGCCCTT  CAGCTTCAGG  CCCGCACTCT  CAGCGATTTG      60
TGTGAATCAT  CTCTGTACAG  TGGGTCGAGA  AAAGGAAGAG  GATGTGGCTC  TAGGGGACTT     120
CAAAAGCCAC  CATTTGAAGG  ACAAGATTCT  GGCCTGTGCT  TCTGAGAGGA  TGCCGCGATT     180
CCTAGGCAGC  GCCCCCACCC  TCACCCAGAC  CTGCCAAACG  CTTCTGGAAG  GATCCGAGGC     240
CTCAGCTCGT  CGCGTGGCGG  GTGTAGGCCC  ACCTCGGTGC  TGGCTGATCC  TAGGGAGATG     300
TTAGGGCTCC  CTGCCCTCGC  AGGCCCTATG  GCTATGCCAC  ACCCACCTCT  AATTCCCTCC     360
ACTCCCACTT  TATTGGCCTT  TTCCTTCCCA  GGTGGCTTCT  ACATGCTCCT  GGACCCCAAG     420
AATGCAAAAC  CAAGGCAAAG  ATCTGCCCTC  CTGAGCCCTC  TGATCCAGTC  CTCCGGCTGC     480
CTGAGCCTGT  CCTTTCAGTA  CACCCAACGT  GGCCAGGCGT  CTGGTGCAAC  CCTCATGGTC     540
TATGCTTCTG  TTTTGGGCAG  CATCCGGAAA  CACACTCTTT  TCTCAGGACA  ACCCGGACCC     600
AGTTGGCAGC  CTGTTTCTGT  CAATTACACA  AGCCAAGGAC  AGATTCAGTT  CACCCTGGTG     660
GGTGTGTTTG  GAAAGATCCC  AGAGCCAGCT  GTGGCAGTAG  ATGCAATCAG  CATTGCTCCC     720
TGTGAAGAGA  GCTTTCCTCA  GTGTGACTTT  GAAGATAATG  CCCATCCCTT  CTGTGACTGG     780
GTACAGGCAT  CACAGGATGG  TGGATACTGG  AGGCAGGGAA  ATAAAAATAC  ATTCATCCAG     840
CCTGCAGGCC  CCTTTGGAAT  CTCCCTTAAT  GGAGAAGGTC  ACTACATCTT  CCTTGAGACT     900
GACAAGTTCT  CCCAGGCAGG  CCAGTCTTTC  AGACTGGTGA  GCCGGCCCTT  CTGTGCCCCG     960
GCTGTGATCT  GCGTGACGTT  TACCTACCAC  ATGTATGGCC  TGGGACAGGG  CACAAAGCTC    1020
AGGCTGCTGC  TGGGGAGTCC  TGCGGGTAGT  CCCCCAAGTT  CTCTCTGGGA  ACGTGTTGGG    1080
CCTCAGAGCC  CTGAATGGCT  GAACACCTCC  GTCACCATCC  CTTCAGGACA  TCAACAGCCC    1140
ATGCAGCTGA  TATTTGAAGC  CGTCAGGGGC  ACCAACACCG  CCTTTGTTGT  TGCTCTGGGT    1200
TTCGTCTTGA  TCAATCATGG  GACCTGTCGA  GGACCTTCTG  AAACCTCTGT  CTCCACAGAA    1260
AAACCCGTGG  CCCCTACAGA  AAAACCAACT  GTCCCAGTG   AAATATACAC  TATCCCCACA    1320
GAAAAGCCCA  TGGTCCACAT  GGAGAAGCCC  ATTGTACACA  CTGAAAAACC  TACAGTTCCC    1380
ACAGAAAAAC  CTACAATCCC  AACAGAAAAA  TCTACAGTGC  CACCAAAAA   ACCCACTGTC    1440
TTTAAAGAAC  CCACCCTTCC  ACCTGAAGGG  CCCACCGTCC  CTGCTGAACG  GCCTACCACC    1500
CCGCCTGAAG  GGCCTGCTGT  CCCTCCTAAA  GGGCCCACTG  TCCTCACTGA  ATGGCCCACA    1560
AGCCACACAG  AAAAATCTAC  TGTCCACACA  GAGAAACCCA  TTCTCCCCAC  AGGAAAATCC    1620
ACCATCCCCA  CAGAAAAACC  CATGGTCCCC  ACCAAAGGA   CCACCACTCC  CACTGAAAGG    1680
ACCACTATCC  CCGCAGAAAA  GCCAACTGTC  CCCATAGAAA  AACCAATGGT  CCCCACCGAA    1740
AGGACCACCA  TTCCCACTGA  AAGAACCACT  ATCCCCACAG  AAAAACCTAC  TGTTCCCACA    1800
GAAAAACTCA  CTGTCCCCAC  AGAAAAGCCA  ATTGTCCCCA  CAGAAAAGCC  GATTGTCCCC    1860
ACAGAAAAAC  ACACCATCCC  CACAGAAAAA  CTGACAGTCC  TCACTGAGAG  GACCACTACT    1920
CCCACTGAAA  GAACCACTAT  CCCCACAGAA  AAACCTACTG  TCCCCACAGA  AAAACCCTCT    1980
GTCCCCACAG  AAAAGCCAAC  TGTCCCCACA  GAAGAACCCA  CCATCCCCAC  AGAAAAGCTT    2040
```

```
ACCGTCCCCA CTGAGAGGAC CACCACTCCC ACCAAAAGGA CCACCACTCC CACCATAAGG   2100
ACCACCACCC CCACCATAAG GACCACCACC CCCACCGAAA GGACCACCAC CCCCACCATA   2160
AGGACCACCA CTCCCACTGA AAGGACCACC ATCCCACGA AAAAGACCAC TGTTCCCACA    2220
GAAAAAACCA TTATCCCCAC TGAAAGGACC ATAGCTCCTA CAACACCCCA GCCCAGCCCA   2280
ACTCTTGTAC CCACTCAGCC AGCAGCCGTC GTGATGCCAA GTACTTCCGC GACCACTGTG   2340
ACCCCGAGAA CTACTATAGC GAGCTGCCCC CCAAATGCCC ACTTTGAACG CTGCGCCTGC   2400
CCAGTGTCCT GCCAGAGCCC CACACCCAAC TGTGAGCTCT TCTGCAAGCC CGGCTGTGTC   2460
TGTGATCCTG GCTTTTTATT CAGTGGCTCC CACTGCGTCA ACGCCTCTTC CTGTGATTGC   2520
TTCTACAACG ACAATTACTA TAAGCTGGGG ACAGATTGGT TCAGCCCCAA CTGCACAGAA   2580
CATTGCCACT GCCGGCCCAG CAGTCGGATG GAGTGCCAGA CCTTCAAGTG CGGGACACAC   2640
ACAGTGTGCC AGCTGAAGAA TGGCCAGTAC GGCTGCCACC CCTATGGCAG TGCCACCTGC   2700
TCTGTCTACG GAGACCCTCA CTACCTCACC TTCGACGGGA GGCGCTTTAA CTTCATGGGC   2760
AAGTGCACCT ACATCTTGGC CCAACCCTGT GGCAACTTGA CAGAGCACTT CTTCAGGGTG   2820
CTGGTGAAGA AGGAGGAGCG AGGACAGGAG GGCGTGTCCT GCCTAAGCAA GGTCTACGTG   2880
ACTCTGCCTG AAAGCACCGT CACTCTGCTC AAGGGCAGAC ACACGCTGGT CGGAGGTCAG   2940
CGAGTCACCC TCCCAGCCAT ACCTTCTAGA GGTGTCTTCC TGGCTCCCAG TGGGCGATTT   3000
GTGGAGCTGC AGACGGCGTT CGGTCTGCGG GTGAGATGGG ATGGTGACCA GCAGCTGTTT   3060
GTGAGTGTGC CCAGCACCTT CTCTGGCAAA CTCTGTGGTC TCTGTGGCGA CTATGACGGT   3120
GACAGCAGCA ACGACAACCA GAAGCCGGAT GGCAGTCCAG CAAAAGATGA GAAGGAGCTG   3180
GGTAGCAGCT GGCAGACCTC GGAGGATGCG GACCAGCAGT GCGAGGAGAA CCAGGTGTCT   3240
CCCCCGTCTT GCAACACGGC CTTGCAGAAT ACTATGTCGG GGCCAGAGTT CTGTGGACAG   3300
CTGGTGGCCC CTCATGGAGT CTTCGAGGCG TGCCTGCCTC ACCTCAGGGC CTCTTCCTTC   3360
TTCAAGAGCT GCACGTTTGA CATGTGTAAC TTCCAGGGGC TGCAGCATAT GCTGTGTGCT   3420
CACATGTCGG CCTTGACTGA GAACTGCCAG GATGCTGGCT ACACGGTGAA GCCCTGGAGA   3480
GGACCCCAGT TCTGCCCGCT GGCCTGCCCC CGCAACAGTA GGTACGCT GTGTGCCAGG    3540
CTGTGCCCCG ACACCTGCCA TTCTGAGTTC TCGGGCAGGG CCTGCAAGGA CCGCTGCGTG   3600
GAGGGCTGCG AGTGCGACCC AGGCTTCGTC CTCAGTGGCC TCCAGTGCGT CTCCCGGTCC   3660
GAGTGTGGCT GCCTCGACTC CACAGCGGGT TATGTCAAGG TAGGGGAGCG GTGGTTCAAG   3720
CCAGGCTGCA GACAGCTCTG TATCTGTGAG GGTAACAACA GAACTCGCTG TGTGCTCTGG   3780
AGGTGCCAGG CCCAGGAGTT CTGCGGTCAG CAGGATGGCA TCTACGGCTG CCATGCTCAA   3840
GGGTCTGCCA CCTGCACTGT CTCGGGGGAC CCCCACTACC TGACGTTCGA CGGAGCCCTG   3900
CACCACTTCA CGGGCACCTG CACCTACACC CTGACCAAAC CTTGCTGGCT GAGGTCCCTA   3960
GAGAATTCTT TCCTTGTGAG TGCCACCAAT GAGTTCCGCG GTGGAAATTT AGAGGCCTCC   4020
TACGTCAGAG CCGTCCAGGT GCAGGTCTTC AACCTCAGAA TCTCGCTGAT CAAAGGCCGC   4080
AAAGTCACGC TGGATGGCCG CAGGGTGGCC TTGCCCCTGT GGCCCGCACA AGGCCGGGTG   4140
AGCATCACGT CCAGTGGCTC CTTCATCCTC CTCTACACGG ACTTTGGGCT TCAAGTTCGC   4200
TATGATGGCG ACCACCTGGT GGAAGTGACC GTGCCCTCCT CCTACGCTGG CCGGCTCTGT   4260
GGGCTCTGCG GAACTACAA CAACAACAGC CTGGACGACA TTCTGCAGCC TGATAAAAGG   4320
CCTGCAAGCA GCTCTGTGCG CCTGGGGGCC TCCTGGAAGA TAAATGAGTT ATCTGAACCT   4380
GGCTGCTTTG CTGAAGGTGG CAAGCCCCCC AGGTGCCTGG GAAGGAAGT GGCAGACGCC   4440
```

```
TGGCGTAAGA ACTGTGATGT CTTAATGAAC CCTCAGGGAC CCTTCTCTCA ATGCCACAGG    4500
GTGGTGGCCC CTCAATCCAG CTTCTCCAGC TGTTTGTATG GCCAGTGTGC GACCAAGGGG    4560
GACACCCTGA CCCTGTGCCG CTCCCTGCAG GCCTACGCGT CCCTGTGCGC GCGCGCTGGC    4620
CAGGCCCTCA CCTGGCGGAA TGGCACCTTC TGCCCTCTGA AGTGCCCGTC AGGCAGCAGC    4680
TATAGCACCT GTGCCAACCC CTGCCCAGCC ACCTGCCTCA GCCTGAACAA TCCATCATAC    4740
TGCCCATCCA CGCTGCCCTG TGCCGAGGGC TGCGAGTGCC AGAAAGGCCA CATCTTGAGC    4800
GGAACCTCCT GCGTGCCCCT CAGCCAGTGT GGCTGCACCA CCCAGAGGGG CTCCTACCAC    4860
CCGGTTGGGG AGAGCTGGTA CACGGACAAC AGCTGCTCCA GGCTCTGCAC CTGCTCTGCC    4920
CACAACAACA TCTCCTGCCG CCAGGCCTCC TGCAAGCCCA GCCAGATGTG CTGGCCCCAG    4980
GATGGGCTGA TACGGTGCCG GGTGGCAGGG ATGGGAGTGT GCCGCATCCC TGACACATCC    5040
CACTACGTGA GCTTCGATGG CAGCTACCAT GCTGTCAGGG CAACTGCAC TTACGTCCTG      5100
GTGAAAATAT GCCACTCCAC CATGGACCTG CCTTTCTTCA AGATCAGTGG CGAGAATGGG    5160
AAGCGGGAAG GCCAACCCCC GGCTTTCTAC CTCCGCCAGG TCTACGTGGA TATCTTTAAT    5220
ACCCTGGTCA CCCTGAAACA GGACCAAGTG CTGATCAATG GCACACGGGT CAGTCTGCCT    5280
GCAACCACGC AGATCCGTGG GGTCAGAGTC ATTTCCAGGG ACGGCTACAC CGTGCTCACC    5340
ATCAACATCG GGGTGCAGGT CAAGTTTGAC GGCAGAGGTT TCCTTGAGGT TGAAATCCCC    5400
AAAGCCTATT ACGGAAGGAC CTGCGGCGTG TGCGGGAACT TCAACGACGA GGAAGAAGAC    5460
GAGCTCATGA TGCCCAGTGA TGCACTAGCT CTGGATGACG TCATGTATGT GGACAGCTGG    5520
CGAGATAAGG AGATCGACCC AAATTGCCAG GAAGATGACA GGAAGACCGA AGCAGAATCG    5580
CAAGAGCAGC CAAGTGCAAA CTGCAGGCCA GCTGACCTGG AGCGAGCCCA GGAGCAGTGC    5640
CAGGCGGCCT TTCAGGCCCC GGCCTGGGCA AACTGTGCCA CCCGCGTGGT GCTCAGTCCC    5700
TACGTGCGCA GCTGTACTCA CAAGCTCTGT GAGTTTGGAG GCCTAAACCG TGCCTTTTGC    5760
GAGTCTCTGC AAGCCTTCGG GGCCGCCTGC CAGGCCCAGG GGATCAAGCC CCCAGTCTGG    5820
AGAAACAGCA GCTTCTGCCC TCTGGACTGC TCCGCCCACA GCGTCTACAC CTCCTGCGTC    5880
CCCTCCTGCC TCCCTTCCTG CCAGGACCCC GAAGGCCAGT GCACAGGCGC CGGAGCTCCC    5940
TCCACCTGTG AGGAGGGCTG CATTTGTGAG CCCGGCTACG TGCTCAGCGA GCAGCAGTGT    6000
GTGGCCAGGA GTCAGTGCGG CTGCAGGGAC GCCAGGGGCA CTTTCCTTCC CGTGGGTAGG    6060
TTCCGGCTCT CCAGCGGCTG CTCCCAGATG TGTGTCTGCA CAGCGGGAGC CATTGAGTGC    6120
AGGCCCTTCA CCTGCCCCTC CGGCTCCCAG TGCGAGCCCA ACGAAGACGG CAAGGACTTC    6180
TGCCAACCCA ACAGCTCCAA TCTATGCTCA GTTTTCGGGG ATCCCCATTA CCGCACATTT    6240
GATGGCCTCA GCTACCGCTT CCAGGGCCGC ATGACCTACA CCCTGGTCAA GACCTTGGAC    6300
GTGCTCCCCG ATGGGGTGGA GCCCTGGTG GTGGAGGGAC GCAACAAGGT GTATCCATCC     6360
TTAACCCCGG TCTTCCTGCA AGAGATCATC GTCATGGTCT ACGGCTACAC AGTCCAGCTC    6420
CAGGCCGAAC TGGAGCTTGT GGTCAACGGT CAGAAGGTGT CCATCCCCTA CAAGCCCAAC    6480
GAGTACCTGC AGGTCACTCT GCGAGGCCGT CGCCTGTATC TGGTCACAGA CTTTGAGCTG    6540
GTCGTCAGCT TCAATGGAAG AAACAATGCA GTGATCGCCA TGCCCAGCAC CTACCTGGGG    6600
CTCGTGCGAG GCCTGTGCGG CAACTACGAC AAGAACAAGA GGAATGACTT CATGCTGCCT    6660
AATGGCTCCT TCACCCAGAA CCTCCTTGTC TTTGGCAACA GCTGGGAGGT AAAGGCCAAG    6720
GAAGGCCACC CCCGCTTCTC AAGGGCCATT CGAGAGGAGG AAGAGAAAAA CGAAGAGTCA    6780
GGCTTTCAGA ATGTGTCAGA ATGCAGCCCA GAGCAGCTGG AGCTCGTCAA CCACACCCAG    6840
```

| | | | | |
|---|---|---|---|---|
| GCGTGTGGGG | TGCTGGTGGA | CCCTCAGGGC | CCCTTTGCTG | CCTGTCACCA | GATTGTGGCC | 6900 |
| CCAGGGCCCT | TCCAGGAGCA | CTGTGTGTTT | GATCTCTGTG | CTGCCCCGGG | CCCCAAAGAG | 6960 |
| CAGGAGGAGT | TGCGTTGCCA | GGTCCTCAGC | GGGTACGCCA | TCATCTGCCA | GGAGTCGGGG | 7020 |
| CCCACCCTGG | CCGGCTGGCG | GGACCACACC | CACTGCGCCT | TGCCATGTCC | GGCCAACACG | 7080 |
| GTCTATCAGA | GCTGTATGAC | ACCCTGCCCA | GCCTCCTGTG | CCACCCTGGC | AGTCCCCCGG | 7140 |
| GCCTGCGACG | GCCCGTGTGT | GGAGGGCTGT | GCCAGCCTCC | CCGGTTACAT | CTACAGTGGT | 7200 |
| GCCCAGAGCC | TTCCCATGGC | CCACTGTGGC | TGCACCAACA | ACGGCGTCTA | CTACCAGCAG | 7260 |
| GGTGACAGCT | TCGTGACCGA | GAACTGCTCT | CAGCGCTGCA | CCTGTGCCAG | CTCGGGGGTC | 7320 |
| CTGCTGTGTG | AGCCCCTCAG | CTGCCGCCCT | GGGGAGATCT | GCACCCTGGG | GAACCTCACT | 7380 |
| CGTGGCTGCT | TCCGAGACAG | CCCATGTCTA | CAGAACCCCT | GTCAGAATGA | TGGGCGGTGT | 7440 |
| CGGGAGCAGG | GAACCCACTT | CACCTGTGAG | TGTGAACTTG | GTTACGGGGG | AGACCTCTGC | 7500 |
| ACGGAGCCTC | GGGGTGTACC | ATCCCCCAAA | AAGCCAGAGG | CGTCCAACCG | CGTGGCCATC | 7560 |
| CTCTTGGGGA | TGCTGATGCC | CACAGTGCTC | CTGGTGCCGG | CGGTGACCAG | AGTTTCCAGG | 7620 |
| AAGAGGAGGA | GGAGGAGGAG | GCCCTCTAGG | GAGAGAACGC | AGAGCCAGAA | CAGAGGCAAG | 7680 |
| CGGGCCGGCA | CAGATTGTGC | TCCAGAGCAG | GCCTACAAAG | TGGCTTAGTT | TTGAGGTGTT | 7740 |
| CACACAAAGG | GAGAGATAAA | ATTATTTATT | TTTGAAAAAA | AAAAA | | 7785 |

(2) INFORMATION FOR SEQ ID NO:2:

(i) SEQUENCE CHARACTERISTICS:
        (A) LENGTH: 2476 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:2:

```
Met Leu Gly Leu Pro Ala Leu Ala Gly Pro Met Ala Met Pro His Pro
  1               5                  10                  15

Pro Leu Ile Pro Ser Thr Pro Thr Leu Leu Ala Phe Ser Phe Pro Gly
             20                  25                  30

Gly Phe Tyr Met Leu Leu Asp Pro Lys Asn Ala Lys Pro Arg Gln Arg
         35                  40                  45

Ser Ala Leu Leu Ser Pro Leu Ile Gln Ser Ser Gly Cys Leu Ser Leu
     50                  55                  60

Ser Phe Gln Tyr Thr Gln Arg Gly Gln Ala Ser Gly Ala Thr Leu Met
 65                  70                  75                  80

Val Tyr Ala Ser Val Leu Gly Ser Ile Arg Lys His Thr Leu Phe Ser
                 85                  90                  95

Gly Gln Pro Gly Pro Ser Trp Gln Pro Val Ser Val Asn Tyr Thr Ser
            100                 105                 110

Gln Gly Gln Ile Gln Phe Thr Leu Val Gly Val Phe Gly Lys Ile Pro
        115                 120                 125

Glu Pro Ala Val Ala Val Asp Ala Ile Ser Ile Ala Pro Cys Glu Glu
    130                 135                 140

Ser Phe Pro Gln Cys Asp Phe Glu Asp Asn Ala His Pro Phe Cys Asp
145                 150                 155                 160

Trp Val Gln Ala Ser Gln Asp Gly Gly Tyr Trp Arg Gln Gly Asn Lys
                165                 170                 175

Asn Thr Phe Ile Gln Pro Ala Gly Pro Phe Gly Ile Ser Leu Asn Gly
```

```
                              180                     185                     190
        Glu  Gly  His  Tyr  Ile  Phe  Leu  Glu  Thr  Asp  Lys  Phe  Ser  Gln  Ala  Gly
                       195                      200                 205
        Gln  Ser  Phe  Arg  Leu  Val  Ser  Arg  Pro  Phe  Cys  Ala  Pro  Ala  Val  Ile
             210                      215                      220
        Cys  Val  Thr  Phe  Thr  Tyr  His  Met  Tyr  Gly  Leu  Gly  Gln  Gly  Thr  Lys
        225                      230                      235                      240
        Leu  Arg  Leu  Leu  Leu  Gly  Ser  Pro  Ala  Gly  Ser  Pro  Pro  Ser  Ser  Leu
                            245                      250                      255
        Trp  Glu  Arg  Val  Gly  Pro  Gln  Ser  Pro  Glu  Trp  Leu  Asn  Thr  Ser  Val
                       260                      265                      270
        Thr  Ile  Pro  Ser  Gly  His  Gln  Gln  Pro  Met  Gln  Leu  Ile  Phe  Glu  Ala
                  275                      280                      285
        Val  Arg  Gly  Thr  Asn  Thr  Ala  Phe  Val  Val  Ala  Leu  Gly  Phe  Val  Leu
             290                      295                      300
        Ile  Asn  His  Gly  Thr  Cys  Arg  Gly  Pro  Ser  Glu  Thr  Ser  Val  Ser  Thr
        305                      310                      315                      320
        Glu  Lys  Pro  Val  Ala  Pro  Thr  Glu  Lys  Pro  Thr  Val  Pro  Ser  Glu  Ile
                            325                      330                      335
        Tyr  Thr  Ile  Pro  Thr  Glu  Lys  Pro  Met  Val  His  Met  Glu  Lys  Pro  Ile
                       340                      345                      350
        Val  His  Thr  Glu  Lys  Pro  Thr  Val  Pro  Thr  Glu  Lys  Pro  Thr  Ile  Pro
                  355                      360                      365
        Thr  Glu  Lys  Ser  Thr  Val  Pro  Thr  Lys  Lys  Pro  Thr  Val  Phe  Lys  Glu
             370                      375                      380
        Pro  Thr  Leu  Pro  Pro  Glu  Gly  Pro  Thr  Val  Pro  Ala  Glu  Arg  Pro  Thr
        385                      390                      395                      400
        Thr  Pro  Pro  Glu  Gly  Pro  Ala  Val  Pro  Pro  Lys  Gly  Pro  Thr  Val  Leu
                            405                      410                      415
        Thr  Glu  Trp  Pro  Thr  Ser  His  Thr  Glu  Lys  Ser  Thr  Val  His  Thr  Glu
                       420                      425                      430
        Lys  Pro  Ile  Leu  Pro  Thr  Gly  Lys  Ser  Thr  Ile  Pro  Thr  Glu  Lys  Pro
                  435                      440                      445
        Met  Val  Pro  Thr  Lys  Arg  Thr  Thr  Pro  Thr  Glu  Arg  Thr  Thr  Ile
             450                      455                      460
        Pro  Ala  Glu  Lys  Pro  Thr  Val  Pro  Ile  Glu  Lys  Pro  Met  Val  Pro  Thr
        465                      470                      475                      480
        Glu  Arg  Thr  Thr  Ile  Pro  Thr  Glu  Arg  Thr  Ile  Pro  Thr  Glu  Lys
                            485                      490                      495
        Pro  Thr  Val  Pro  Thr  Glu  Lys  Leu  Thr  Val  Pro  Thr  Glu  Lys  Pro  Ile
                       500                      505                      510
        Val  Pro  Thr  Glu  Lys  Pro  Ile  Val  Pro  Thr  Glu  Lys  His  Thr  Ile  Pro
                  515                      520                      525
        Thr  Glu  Lys  Leu  Thr  Val  Leu  Thr  Glu  Arg  Thr  Thr  Pro  Thr  Glu
             530                      535                      540
        Arg  Thr  Thr  Ile  Pro  Thr  Glu  Lys  Pro  Thr  Val  Pro  Thr  Glu  Lys  Pro
        545                      550                      555                      560
        Ser  Val  Pro  Thr  Glu  Lys  Pro  Thr  Val  Pro  Thr  Glu  Glu  Pro  Thr  Ile
                            565                      570                      575
        Pro  Thr  Glu  Lys  Leu  Thr  Val  Pro  Thr  Glu  Arg  Thr  Thr  Pro  Thr
                       580                      585                      590
        Lys  Arg  Thr  Thr  Thr  Pro  Thr  Ile  Arg  Thr  Thr  Thr  Pro  Thr  Ile  Arg
                  595                      600                      605
```

```
Thr Thr Thr Pro Thr Glu Arg Thr Thr Thr Pro Thr Ile Arg Thr Thr
    610             615                 620

Thr Pro Thr Glu Arg Thr Thr Ile Pro Thr Lys Lys Thr Thr Val Pro
625             630              635                     640

Thr Glu Lys Thr Ile Ile Pro Thr Glu Arg Thr Ile Ala Pro Thr
            645                 650                     655

Pro Gln Pro Ser Pro Thr Leu Val Pro Thr Gln Pro Ala Ala Val Val
            660             665                 670

Met Pro Ser Thr Ser Ala Thr Thr Val Thr Pro Arg Thr Thr Ile Ala
            675             680             685

Ser Cys Pro Pro Asn Ala His Phe Glu Arg Cys Ala Cys Pro Val Ser
    690                 695             700

Cys Gln Ser Pro Thr Pro Asn Cys Glu Leu Phe Cys Lys Pro Gly Cys
705             710                 715                     720

Val Cys Asp Pro Gly Phe Leu Phe Ser Gly Ser His Cys Val Asn Ala
            725             730                 735

Ser Ser Cys Asp Cys Phe Tyr Asn Asp Tyr Tyr Lys Leu Gly Thr
            740             745                 750

Asp Trp Phe Ser Pro Asn Cys Thr Glu His Cys His Cys Arg Pro Ser
        755             760                 765

Ser Arg Met Glu Cys Gln Thr Phe Lys Cys Gly Thr His Thr Val Cys
770                 775                 780

Gln Leu Lys Asn Gly Gln Tyr Gly Cys His Pro Tyr Gly Ser Ala Thr
785             790                 795                     800

Cys Ser Val Tyr Gly Asp Pro His Tyr Leu Thr Phe Asp Gly Arg Arg
            805             810                     815

Phe Asn Phe Met Gly Lys Cys Thr Tyr Ile Leu Ala Gln Pro Cys Gly
            820             825                 830

Asn Leu Thr Glu His Phe Phe Arg Val Leu Val Lys Lys Glu Glu Arg
            835             840             845

Gly Gln Glu Gly Val Ser Cys Leu Ser Lys Val Tyr Val Thr Leu Pro
850             855                 860

Glu Ser Thr Val Thr Leu Leu Lys Gly Arg His Thr Leu Val Gly Gly
865             870                 875                     880

Gln Arg Val Thr Leu Pro Ala Ile Pro Ser Arg Gly Val Phe Leu Ala
            885                 890                 895

Pro Ser Gly Arg Phe Val Glu Leu Gln Thr Ala Phe Gly Leu Arg Val
            900             905             910

Arg Trp Asp Gly Asp Gln Gln Leu Phe Val Ser Val Pro Ser Thr Phe
        915             920             925

Ser Gly Lys Leu Cys Gly Leu Cys Gly Asp Tyr Asp Gly Asp Ser Ser
    930             935             940

Asn Asp Asn Gln Lys Pro Asp Gly Ser Pro Ala Lys Asp Glu Lys Glu
945             950             955                     960

Leu Gly Ser Ser Trp Gln Thr Ser Glu Asp Ala Asp Gln Gln Cys Glu
            965             970             975

Glu Asn Gln Val Ser Pro Pro Ser Cys Asn Thr Ala Leu Gln Asn Thr
            980             985                 990

Met Ser Gly Pro Glu Phe Cys Gly Gln Leu Val Ala Pro His Gly Val
        995             1000                1005

Phe Glu Ala Cys Leu Pro His Leu Arg Ala Ser Ser Phe Phe Lys Ser
        1010            1015            1020

Cys Thr Phe Asp Met Cys Asn Phe Gln Gly Leu Gln His Met Leu Cys
1025            1030            1035                    1040
```

```
Ala His Met Ser Ala Leu Thr Glu Asn Cys Gln Asp Ala Gly Tyr Thr
                    1045                1050                1055

Val Lys Pro Trp Arg Gly Pro Gln Phe Cys Pro Leu Ala Cys Pro Arg
            1060                1065                1070

Asn Ser Arg Tyr Thr Leu Cys Ala Arg Leu Cys Pro Asp Thr Cys His
            1075                1080                1085

Ser Glu Phe Ser Gly Arg Ala Cys Lys Asp Arg Cys Val Glu Gly Cys
        1090                1095                1100

Glu Cys Asp Pro Gly Phe Val Leu Ser Gly Leu Gln Cys Val Ser Arg
1105                1110                1115                1120

Ser Glu Cys Gly Cys Leu Asp Ser Thr Ala Gly Tyr Val Lys Val Gly
                1125                1130                1135

Glu Arg Trp Phe Lys Pro Gly Cys Arg Gln Leu Cys Ile Cys Glu Gly
            1140                1145                1150

Asn Asn Arg Thr Arg Cys Val Leu Trp Arg Cys Gln Ala Gln Glu Phe
            1155                1160                1165

Cys Gly Gln Gln Asp Gly Ile Tyr Gly Cys His Ala Gln Gly Ser Ala
        1170                1175                1180

Thr Cys Thr Val Ser Gly Asp Pro His Tyr Leu Thr Phe Asp Gly Ala
1185                1190                1195                1200

Leu His His Phe Thr Gly Thr Cys Thr Tyr Thr Leu Thr Lys Pro Cys
                1205                1210                1215

Trp Leu Arg Ser Leu Glu Asn Ser Phe Leu Val Ser Ala Thr Asn Glu
            1220                1225                1230

Phe Arg Gly Gly Asn Leu Glu Ala Ser Tyr Val Arg Ala Val Gln Val
            1235                1240                1245

Gln Val Phe Asn Leu Arg Ile Ser Leu Ile Lys Gly Arg Lys Val Thr
        1250                1255                1260

Leu Asp Gly Arg Arg Val Ala Leu Pro Leu Trp Pro Ala Gln Gly Arg
1265                1270                1275                1280

Val Ser Ile Thr Ser Ser Gly Ser Phe Ile Leu Leu Tyr Thr Asp Phe
                1285                1290                1295

Gly Leu Gln Val Arg Tyr Asp Gly Asp His Leu Val Glu Val Thr Val
            1300                1305                1310

Pro Ser Ser Tyr Ala Gly Arg Leu Cys Gly Leu Cys Gly Asn Tyr Asn
            1315                1320                1325

Asn Asn Ser Leu Asp Asp Ile Leu Gln Pro Asp Lys Arg Pro Ala Ser
            1330                1335                1340

Ser Ser Val Arg Leu Gly Ala Ser Trp Lys Ile Asn Glu Leu Ser Glu
1345                1350                1355                1360

Pro Gly Cys Phe Ala Glu Gly Gly Lys Pro Pro Arg Cys Leu Gly Lys
                1365                1370                1375

Glu Val Ala Asp Ala Trp Arg Lys Asn Cys Asp Val Leu Met Asn Pro
            1380                1385                1390

Gln Gly Pro Phe Ser Gln Cys His Arg Val Val Ala Pro Gln Ser Ser
            1395                1400                1405

Phe Ser Ser Cys Leu Tyr Gly Gln Cys Ala Thr Lys Gly Asp Thr Leu
            1410                1415                1420

Thr Leu Cys Arg Ser Leu Gln Ala Tyr Ala Ser Leu Cys Ala Arg Ala
1425                1430                1435                1440

Gly Gln Ala Leu Thr Trp Arg Asn Gly Thr Phe Cys Pro Leu Lys Cys
                1445                1450                1455

Pro Ser Gly Ser Ser Tyr Ser Thr Cys Ala Asn Pro Cys Pro Ala Thr
```

|      |      |      |      |      |      |      |      |      |      |      |      |      |      |      |
|---|---|---|---|---|---|---|---|---|---|---|---|---|---|---|
|      |      |      |      | 1460 |      |      |      | 1465 |      |      |      | 1470 |      |      |
| Cys  | Leu  | Ser  | Leu  | Asn  | Asn  | Pro  | Ser  | Tyr  | Cys  | Pro  | Ser  | Thr  | Leu  | Pro  | Cys |
|      |      | 1475 |      |      |      |      | 1480 |      |      |      |      | 1485 |      |      |
| Ala  | Glu  | Gly  | Cys  | Glu  | Cys  | Gln  | Lys  | Gly  | His  | Ile  | Leu  | Ser  | Gly  | Thr  | Ser |
|      |      | 1490 |      |      |      |      | 1495 |      |      |      |      | 1500 |      |      |
| Cys  | Val  | Pro  | Leu  | Ser  | Gln  | Cys  | Gly  | Cys  | Thr  | Thr  | Gln  | Arg  | Gly  | Ser  | Tyr |
| 1505 |      |      |      |      | 1510 |      |      |      |      | 1515 |      |      |      |      | 1520 |
| His  | Pro  | Val  | Gly  | Glu  | Ser  | Trp  | Tyr  | Thr  | Asp  | Asn  | Ser  | Cys  | Ser  | Arg  | Leu |
|      |      |      |      | 1525 |      |      |      |      | 1530 |      |      |      |      | 1535 |     |
| Cys  | Thr  | Cys  | Ser  | Ala  | His  | Asn  | Asn  | Ile  | Ser  | Cys  | Arg  | Gln  | Ala  | Ser  | Cys |
|      |      |      |      | 1540 |      |      |      |      | 1545 |      |      |      |      | 1550 |     |
| Lys  | Pro  | Ser  | Gln  | Met  | Cys  | Trp  | Pro  | Gln  | Asp  | Gly  | Leu  | Ile  | Arg  | Cys  | Arg |
|      |      |      |      | 1555 |      |      |      |      | 1560 |      |      |      |      | 1565 |     |
| Val  | Ala  | Gly  | Met  | Gly  | Val  | Cys  | Arg  | Ile  | Pro  | Asp  | Thr  | Ser  | His  | Tyr  | Val |
|      |      |      |      | 1570 |      |      |      |      | 1575 |      |      |      |      | 1580 |     |
| Ser  | Phe  | Asp  | Gly  | Ser  | Tyr  | His  | Ala  | Val  | Arg  | Gly  | Asn  | Cys  | Thr  | Tyr  | Val |
| 1585 |      |      |      |      | 1590 |      |      |      |      | 1595 |      |      |      |      | 1600 |
| Leu  | Val  | Lys  | Ile  | Cys  | His  | Ser  | Thr  | Met  | Asp  | Leu  | Pro  | Phe  | Phe  | Lys  | Ile |
|      |      |      |      | 1605 |      |      |      |      | 1610 |      |      |      |      | 1615 |     |
| Ser  | Gly  | Glu  | Asn  | Gly  | Lys  | Arg  | Glu  | Gly  | Gln  | Pro  | Pro  | Ala  | Phe  | Tyr  | Leu |
|      |      |      |      | 1620 |      |      |      |      | 1625 |      |      |      |      | 1630 |     |
| Arg  | Gln  | Val  | Tyr  | Val  | Asp  | Ile  | Phe  | Asn  | Thr  | Leu  | Val  | Thr  | Leu  | Lys  | Gln |
|      |      |      |      | 1635 |      |      |      |      | 1640 |      |      |      |      | 1645 |     |
| Asp  | Gln  | Val  | Leu  | Ile  | Asn  | Gly  | Thr  | Arg  | Val  | Ser  | Leu  | Pro  | Ala  | Thr  | Thr |
|      |      |      |      | 1650 |      |      |      |      | 1655 |      |      |      |      | 1660 |     |
| Gln  | Ile  | Arg  | Gly  | Val  | Arg  | Val  | Ile  | Ser  | Arg  | Asp  | Gly  | Tyr  | Thr  | Val  | Leu |
| 1665 |      |      |      |      | 1670 |      |      |      |      | 1675 |      |      |      |      | 1680 |
| Thr  | Ile  | Asn  | Ile  | Gly  | Val  | Gln  | Val  | Lys  | Phe  | Asp  | Gly  | Arg  | Gly  | Phe  | Leu |
|      |      |      |      | 1685 |      |      |      |      | 1690 |      |      |      |      | 1695 |     |
| Glu  | Val  | Glu  | Ile  | Pro  | Lys  | Ala  | Tyr  | Tyr  | Gly  | Arg  | Thr  | Cys  | Gly  | Val  | Cys |
|      |      |      |      | 1700 |      |      |      |      | 1705 |      |      |      |      | 1710 |     |
| Gly  | Asn  | Phe  | Asn  | Asp  | Glu  | Glu  | Glu  | Asp  | Glu  | Leu  | Met  | Met  | Pro  | Ser  | Asp |
|      |      |      |      | 1715 |      |      |      |      | 1720 |      |      |      |      | 1725 |     |
| Ala  | Leu  | Ala  | Leu  | Asp  | Asp  | Val  | Met  | Tyr  | Val  | Asp  | Ser  | Trp  | Arg  | Asp  | Lys |
|      |      |      |      | 1730 |      |      |      |      | 1735 |      |      |      |      | 1740 |     |
| Glu  | Ile  | Asp  | Pro  | Asn  | Cys  | Gln  | Glu  | Asp  | Asp  | Arg  | Lys  | Thr  | Glu  | Ala  | Glu |
| 1745 |      |      |      |      | 1750 |      |      |      |      | 1755 |      |      |      |      | 1760 |
| Ser  | Gln  | Glu  | Gln  | Pro  | Ser  | Ala  | Asn  | Cys  | Arg  | Pro  | Ala  | Asp  | Leu  | Glu  | Arg |
|      |      |      |      | 1765 |      |      |      |      | 1770 |      |      |      |      | 1775 |     |
| Ala  | Gln  | Glu  | Gln  | Cys  | Gln  | Ala  | Ala  | Phe  | Gln  | Ala  | Pro  | Ala  | Trp  | Ala  | Asn |
|      |      |      |      | 1780 |      |      |      |      | 1785 |      |      |      |      | 1790 |     |
| Cys  | Ala  | Thr  | Arg  | Val  | Val  | Leu  | Ser  | Pro  | Tyr  | Val  | Arg  | Ser  | Cys  | Thr  | His |
|      |      |      |      | 1795 |      |      |      |      | 1800 |      |      |      |      | 1805 |     |
| Lys  | Leu  | Cys  | Glu  | Phe  | Gly  | Gly  | Leu  | Asn  | Arg  | Ala  | Phe  | Cys  | Glu  | Ser  | Leu |
|      |      |      |      | 1810 |      |      |      |      | 1815 |      |      |      |      | 1820 |     |
| Gln  | Ala  | Phe  | Gly  | Ala  | Ala  | Cys  | Gln  | Ala  | Gln  | Gly  | Ile  | Lys  | Pro  | Pro  | Val |
| 1825 |      |      |      |      | 1830 |      |      |      |      | 1835 |      |      |      |      | 1840 |
| Trp  | Arg  | Asn  | Ser  | Ser  | Phe  | Cys  | Pro  | Leu  | Asp  | Cys  | Ser  | Ala  | His  | Ser  | Val |
|      |      |      |      | 1845 |      |      |      |      | 1850 |      |      |      |      | 1855 |     |
| Tyr  | Thr  | Ser  | Cys  | Val  | Pro  | Ser  | Cys  | Leu  | Pro  | Ser  | Cys  | Gln  | Asp  | Pro  | Glu |
|      |      |      |      | 1860 |      |      |      |      | 1865 |      |      |      |      | 1870 |     |
| Gly  | Gln  | Cys  | Thr  | Gly  | Ala  | Gly  | Ala  | Pro  | Ser  | Thr  | Cys  | Glu  | Glu  | Gly  | Cys |
|      |      |      |      | 1875 |      |      |      |      | 1880 |      |      |      |      | 1885 |     |

```
Ile Cys Glu Pro Gly Tyr Val Leu Ser Glu Gln Gln Cys Val Ala Arg
    1890                1895                1900

Ser Gln Cys Gly Cys Arg Asp Ala Arg Gly Thr Phe Leu Pro Val Gly
1905                1910                1915                1920

Arg Phe Arg Leu Ser Gly Cys Ser Met Cys Val Cys Thr Ala
                1925            1930                1935

Gly Ala Ile Glu Cys Arg Pro Phe Thr Cys Pro Ser Gly Ser Gln Cys
            1940                1945                1950

Glu Pro Asn Glu Asp Gly Lys Asp Phe Cys Gln Pro Asn Ser Ser Asn
        1955                1960                1965

Leu Cys Ser Val Phe Gly Asp Pro His Tyr Arg Thr Phe Asp Gly Leu
        1970                1975                1980

Ser Tyr Arg Phe Gln Gly Arg Met Thr Tyr Thr Leu Val Lys Thr Leu
1985                1990                1995                2000

Asp Val Leu Pro Asp Gly Val Glu Pro Leu Val Val Glu Gly Arg Asn
                2005                2010                2015

Lys Val Tyr Pro Ser Leu Thr Pro Val Phe Leu Gln Glu Ile Ile Val
                2020                2025                2030

Met Val Tyr Gly Tyr Thr Val Gln Leu Gln Ala Glu Leu Glu Leu Val
                2035                2040                2045

Val Asn Gly Gln Lys Val Ser Ile Pro Tyr Lys Pro Asn Glu Tyr Leu
    2050                2055                2060

Gln Val Thr Leu Arg Gly Arg Arg Leu Tyr Leu Val Thr Asp Phe Glu
2065                2070                2075                2080

Leu Val Val Ser Phe Asn Gly Arg Asn Asn Ala Val Ile Ala Met Pro
                2085                2090                2095

Ser Thr Tyr Leu Gly Leu Val Arg Gly Leu Cys Gly Asn Tyr Asp Lys
                2100                2105                2110

Asn Lys Arg Asn Asp Phe Met Leu Pro Asn Gly Ser Phe Thr Gln Asn
            2115                2120                2125

Leu Leu Val Phe Gly Asn Ser Trp Glu Val Lys Ala Lys Glu Gly His
                2130                2135                2140

Pro Arg Phe Ser Arg Ala Ile Arg Glu Glu Glu Glu Lys Asn Glu Glu
2145                2150                2155                2160

Ser Gly Phe Gln Asn Val Ser Glu Cys Ser Pro Glu Gln Leu Glu Leu
                2165                2170                2175

Val Asn His Thr Gln Ala Cys Gly Val Leu Val Asp Pro Gln Gly Pro
            2180                2185                2190

Phe Ala Ala Cys His Gln Ile Val Ala Pro Gly Pro Phe Gln Glu His
                2195                2200                2205

Cys Val Phe Asp Leu Cys Ala Ala Pro Gly Pro Lys Glu Gln Glu Glu
    2210                2215                2220

Leu Arg Cys Gln Val Leu Ser Gly Tyr Ala Ile Ile Cys Gln Glu Ser
2225                2230                2235                2240

Gly Pro Thr Leu Ala Gly Trp Arg Asp His Thr His Cys Ala Leu Pro
                2245                2250                2255

Cys Pro Ala Asn Thr Val Tyr Gln Ser Cys Met Thr Pro Cys Pro Ala
            2260                2265                2270

Ser Cys Ala Thr Leu Ala Val Pro Arg Ala Cys Asp Gly Pro Cys Val
        2275                2280                2285

Glu Gly Cys Ala Ser Leu Pro Gly Tyr Ile Tyr Ser Gly Ala Gln Ser
2290                2295                2300

Leu Pro Met Ala His Cys Gly Cys Thr Asn Asn Gly Val Tyr Tyr Gln
2305                2310                2315                2320
```

```
      Gln  Gly  Asp  Ser  Phe  Val  Thr  Glu  Asn  Cys  Ser  Gln  Arg  Cys  Thr  Cys
                          2325                     2330                     2335

Ala  Ser  Ser  Gly  Val  Leu  Leu  Cys  Glu  Pro  Leu  Ser  Cys  Arg  Pro  Gly
                          2340                     2345                     2350

Glu  Ile  Cys  Thr  Leu  Gly  Asn  Leu  Thr  Arg  Gly  Cys  Phe  Arg  Asp  Ser
                          2355                     2360                     2365

Pro  Cys  Leu  Gln  Asn  Pro  Cys  Gln  Asn  Asp  Gly  Arg  Cys  Arg  Glu  Gln
                          2370                     2375                     2380

Gly  Thr  His  Phe  Thr  Cys  Glu  Cys  Glu  Leu  Gly  Tyr  Gly  Gly  Asp  Leu
      2385                     2390                     2395                     2400

Cys  Thr  Glu  Pro  Arg  Gly  Val  Pro  Ser  Pro  Lys  Lys  Pro  Glu  Ala  Ser
                          2405                     2410                     2415

Asn  Arg  Val  Ala  Ile  Leu  Leu  Gly  Met  Leu  Met  Pro  Thr  Val  Leu  Leu
                          2420                     2425                     2430

Val  Pro  Ala  Val  Thr  Arg  Val  Ser  Arg  Lys  Arg  Arg  Arg  Arg  Arg  Arg
                          2435                     2440                     2445

Pro  Ser  Arg  Glu  Arg  Thr  Gln  Ser  Gln  Asn  Arg  Gly  Lys  Arg  Ala  Gly
                          2450                     2455                     2460

Thr  Asp  Cys  Ala  Pro  Glu  Gln  Ala  Tyr  Lys  Val  Ala
      2465                     2470                     2475
```

( 2 ) INFORMATION FOR SEQ ID NO:3:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( i i ) MOLECULE TYPE: DNA ( i x ) FEATURE:
        ( A ) NAME/KEY: modified_base
        ( B ) LOCATION: 18..30
        ( D ) OTHER INFORMATION: /mod_base=OTHER
            / note= "N = Inosine"

( x i ) SEQUENCE DESCRIPTION: SEQ ID NO:3:

GAATTCGAAT TCGARGGNCA RCCNCCNGCN TTYTAYYT        38

( 2 ) INFORMATION FOR SEQ ID NO:4:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( i i ) MOLECULE TYPE: DNA ( i x ) FEATURE:
        ( A ) NAME/KEY: modified_base
        ( B ) LOCATION: 15..33
        ( D ) OTHER INFORMATION: /mod_base=OTHER
            / note= "N = Inosine"

( x i ) SEQUENCE DESCRIPTION: SEQ ID NO:4:

GGATCCGGAT CCCANGCNGG NGCYTGRAAN GCNGCYTG        38

( 2 ) INFORMATION FOR SEQ ID NO:5:

( i ) SEQUENCE CHARACTERISTICS:
        ( A ) LENGTH: 8 amino acids
        ( B ) TYPE: amino acid
        ( C ) STRANDEDNESS: single

```
            ( D ) TOPOLOGY: linear ( i i ) MOLECULE TYPE: peptide ( x i ) SEQUENCE DESCRIPTION: SEQ ID NO:5:

Val   Thr   Tyr   Ile   Leu   Ala   Gln   Pro
    1                       5

( 2 ) INFORMATION FOR SEQ ID NO:6:

( i ) SEQUENCE CHARACTERISTICS:
            ( A ) LENGTH: 6 amino acids
            ( B ) TYPE: amino acid
            ( C ) STRANDEDNESS: single
            ( D ) TOPOLOGY: linear ( i i ) MOLECULE TYPE: peptide ( x i ) SEQUENCE DESCRIPTION: SEQ ID NO:6:

Leu   Phe   Val   Tyr   Val   Pro
    1                       5

( 2 ) INFORMATION FOR SEQ ID NO:7:

( i ) SEQUENCE CHARACTERISTICS:
            ( A ) LENGTH: 8 amino acids
            ( B ) TYPE: amino acid
            ( C ) STRANDEDNESS: single
            ( D ) TOPOLOGY: linear ( i i ) MOLECULE TYPE: peptide ( x i ) SEQUENCE DESCRIPTION: SEQ ID NO:7:

Xaa   Leu   Gly   Ser   Ser   Tyr   Gln   Thr
    1                       5

( 2 ) INFORMATION FOR SEQ ID NO:8:

( i ) SEQUENCE CHARACTERISTICS:
            ( A ) LENGTH: 10 amino acids
            ( B ) TYPE: amino acid
            ( C ) STRANDEDNESS: single
            ( D ) TOPOLOGY: linear ( i i ) MOLECULE TYPE: peptide ( x i ) SEQUENCE DESCRIPTION: SEQ ID NO:8:

Gly   Gly   Asn   Leu   Glu   Ala   Lys   Tyr   Val   Arg
    1                       5                           1 0
```

SPECIES SPECIFIC EGG-BINDING PROTEINS OF SPERM

The U.S. Government owns rights in the present invention pursuant to grant number 93-37203-9024 from the U.S. Department of Agriculture.

BACKGROUND OF THE INVENTION

1. Field of the Invention

The present invention relates generally to the fields of sperm proteins. More particularly, it provides DNA segments encoding sperm proteins that bind to eggs in a species specific manner, methods of making and using such DNA segments and proteins, methods for detecting sperm and eggs, and methods for inhibiting or promoting their interaction.

2. Description of the Related Art

Mammalian spermatozoa adhere to and then penetrate through the zona pellucida (ZP), an extracellular matrix of the egg; subsequent fusion of the plasma membranes of the gametes completes fertilization (Yanagimachi, 1981). Exocytosis of the sperm acrosome (the acrosome reaction) is one consequence of cellular signaling that occurs during sperm adhesion to the ZP, and is obligatory for sperm penetration of the ZP, possibly because of a requirement for release or exposure of hydrolytic enzymes. Solubilized, conspecific ZP can induce the acrosome reaction in several species (Hardy & Garbers, 1993). Although the sperm surface receptors that transduce the signal for the acrosome reaction have not been identified, receptor-mediated activation of guanine nucleotide-binding regulatory proteins of the Gi class appears to be an important component of the signaling cascade (Hardy & Garbers, 1993; Ward & Kopf, 1993).

Homologous spermatozoa fertilize eggs in vitro more efficiently than heterologous spermatozoa, in part because spermatozoa generally adhere preferentially to conspecific ZP (Yanagimachi, 1981; Peterson et al., 1980; Schmell & Gulyas, 1980). Induction of the acrosome reaction by the ZP is also species-selective (Cherr et al., 1986; Moller et al., 1990; Uto et al., 1988), suggesting that the sperm surface proteins that mediate adhesion and/or signaling bind species-specifically to complementary glycoproteins in the ZP.

The major glycoproteins that comprise the ZP have been characterized for some animals. In the mouse, an Mr 83,000 glycoprotein designated ZP3 possesses both adhesive activity and acrosome reaction-inducing activity; the other ZP glycoproteins (ZP2 and ZP1) may function as structural components that confer the correct spatial context for ZP3 during these processes (Wassarman, 1988). Hamster ZP3 also possesses the adhesive and acrosome reaction-inducing activity of the egg extracellular matrix, and is homologous to mouse ZP3 (Moller et al., 1990; Kinloch et al., 1990). In the pig, a Mr 55,000 glycoprotein of the extracellular matrix, designated ZP3α, appears to account for sperm adhesive activity (Sacco et al., 1989). The amino acid sequences of porcine ZP3α and mouse ZP3 (deduced from the sequences of cloned cDNAs) are not similar (Yurewicz et al., 1993). Hence, different gene products may mediate adhesion of conspecific spermatozoa to the egg extracellular matrix in different species. However, no mammalian sperm molecules have been identified to date that serve as species-specific adhesion ligands.

SUMMARY OF THE INVENTION

The present invention seeks to overcome these and other drawbacks inherent in the prior art by providing DNA segments that encode mammalian sperm proteins that bind to eggs in a species specific manner. Also provided are methods of making and using such DNA segments, proteins and peptides, methods for detecting sperm and eggs, and compositions and methods for inhibiting or promoting the interaction of sperm and eggs.

To delineate the sperm proteins involved in specific adhesion or signaling, the inventors used native, particulate ZP as an affinity matrix to isolate ZP-binding proteins from detergent-solubilized membranes of pig spermatozoa. Two predominant classes of proteins (p105/45 and p56–62) were identified as minor components of the sperm membrane that bind to the egg extracellular matrix in a species-specific manner. This invention also provides DNA segments and vectors that encode the p105/45 sperm adhesion protein.

The invention concerns DNA segments that comprise isolated sperm genes that encode species-specific sperm proteins or peptides, particularly those that include an amino acid sequence essentially as set forth by a contiguous sequence from SEQ ID NO:2, examples of which are those DNA segments that include nucleic acid sequences essentially as set forth by a contiguous sequence from SEQ ID NO:1.

The DNA segments may, of course, comprise sperm genes that encode peptides, such as from about 15 to about 30 or about 50 amino acids in length, or may encode longer proteins, e.g., up to about 2476 amino acids in length, in one exemplary embodiment. Also representative is a DNA segment that comprises a sperm gene that has a nucleic acid sequence as set forth by the sequence of SEQ ID NO:1.

These DNA segments may be positioned under the control of a promoter, and particularly, a recombinant promoter, in order to create a recombinant vector, such as a recombinant expression vector.

Smaller nucleic acid segments are also encompassed, as may be used as probes or primers, such as those that comprises at least a 14 nucleotide long contiguous stretch that corresponds to a nucleic acid sequence of SEQ ID NO:1. Examples include nucleic acid segments with sequences in accordance with SEQ ID NO:3 and SEQ ID NO:4.

The DNA segments may be expressed in a cell system, e.g., by preparing and expressing a recombinant vector in which a species-specific sperm adhesion protein gene DNA segment, such as one that encodes a sperm protein or peptide that includes an amino acid sequence essentially as set forth by a contiguous sequence from SEQ ID NO:2, is positioned under the control of a promoter. One would introduce such a recombinant vector into a recombinant host cell, culture the recombinant host cell under conditions effective to allow expression of an encoded sperm protein or peptide, and then collect the expressed sperm protein or peptide.

The invention thus also provides protein or peptide compositions, free from total sperm cells, that comprise purified species-specific sperm adhesion proteins or peptides, as represented by one that includes an amino acid sequence essentially as set forth by a contiguous sequence from SEQ ID NO:2. Such proteins or peptides may be native or recombinant forms.

The nucleic acids of the present invention may be used in other embodiments, such as in the detection of sperm, or sperm components, in a sample. For example, one may obtain nucleic acids from a sample suspected of containing sperm and contact the nucleic acids with a sperm nucleic acid segment that encodes a species-specific sperm protein or peptide, e.g., one that includes an amino acid sequence essentially as set forth by a contiguous sequence from SEQ ID NO:2. This would be done under conditions effective to allow hybridization of substantially complementary nucleic acids, whereby the hybridized complementary nucleic acids formed could later be detected.

Methods for detecting eggs are also provided, such as may be achieved by contacting a porcine egg with a protein or peptide composition that comprises a purified sperm protein or peptide that includes an amino acid sequence essentially as set forth by a contiguous sequence from SEQ ID NO:2 under conditions effective to allow binding of said protein or peptide to said egg. The presence of proteins or peptides bound to the egg would then be detected.

The interaction of sperm and eggs may also be altered using the present invention, as may be used as part of either contraceptive or fertilization methods. Such methods generally comprise contacting a sperm or egg with an effective amount of a compound that changes the binding of species-specific sperm adhesion protein(s) to the egg. This may be sued to inhibit the interaction of a sperm and an egg, wherein the compound inhibits the binding of the sperm protein to the egg, or to stimulate the interaction of a sperm and an egg, wherein the compound promotes the binding of the sperm protein to the egg.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 2 consists of FIGS. 2A, 2B and 2C, which represent the characterization of disulfide bonding. Shown are two-dimensional SDS-PAGE/Western blots of sperm biotinylated proteins (horizontal dimension, disulfide bonds not reduced; vertical dimension, disulfide bonds reduced). Biotin was detected with horseradish peroxidase-conjugated streptavidin. FIG. 2A: ZP-bound proteins (from 2 μg ZP incubated with detergent-solubilized material from 120 μg sperm membrane proteins) remaining after washing with 1% CHAPS/HNE. FIG. 2B: 2 μg ZP non-binding fraction of sperm proteins. FIG. 2C: ZP-bound proteins (from 2.5 μg ZP incubated with detergent-solubilized material from 50 μg sperm proteins) remaining after washing with 1% CHAPS/HNE and again with mRIPA.

FIG. 4 consists of FIG. 4, Right Panel and FIG. 4, Left Panel, which represent the binding of pig sperm proteins to pig ZP, bovine ZP, or Xenopus oocyte envelopes. Shown are SDS-PAGE/Western blots of sperm biotinylated proteins (detected with horseradish peroxidase-conjugated streptavidin) remaining bound, after washing with 1% CHAPS/HNE, to: Lane 1, 1 μg pig ZP; Lane 2, 0.4 μg bovine ZP; Lane 3, 1 μg Xenopus oocyte envelopes. Lanes 4–6: same as Lanes 1–3, respectively, after washing again with mRIPA. Left panel: disulfide bonds not reduced. Right panel: disulfide bonds reduced.

FIG. 7. Composite nucleotide sequence of overlapping cDNAS cloned using a p105 specific probe and by 5' RACE.

FIG. 8. Deduced sequence and properties of the 2476 residue protein encoded by the 7431 base open reading frame identified in the sequence of the p105/45 message.

FIG. 12, Panel A: hybridization of antisense RNA probe viewed at 40× magnification with dark field illumination. FIG. 12, Panel B: same field, illumination, and exposure as panel A of a parallel section hybridized with a sense RNA probe. FIG. 12, Panel C: Same field as panels A and B of a parallel section stained with hematoxylin and eosin and viewed with bright field illumination. By comparing panels A–C, note that specific hybridization of the antisense RNA probe is strong only in seminiferous tubules. FIG. 12, Panel D: a second field rich in seminiferous tubules hybridized and viewed as panel A. Note than only a small subset of seminiferous tubules expressed high levels of the p105/45 message at the time the tissue was collected. FIG. 12, Panel E: 250× phase contrast view (no counterstain) of two adjacent seminiferous tubules (boxed region of panel D). Note the difference in the level of p105/45 message expression between the two tubules. Expression in the strongly stained tubule is high in spermatids; note the clear zones appearing as halos surrounding the large round nuclei of spermatocytes (arrowheads) that indicate an absence of expression in the cytoplasm of these cells.

DETAILED DESCRIPTION OF THE PREFERRED EMBODIMENTS

Figure 1:
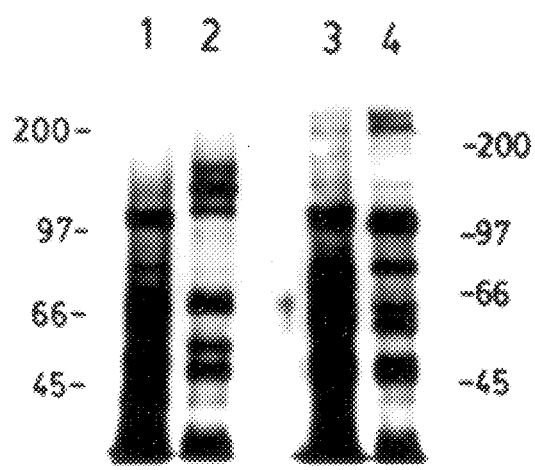
FIG. 1. Identification of ZP-binding proteins. Shown are SDS-PAGE/Western blots of sperm biotinylated proteins (detected with horseradish peroxidase-conjugated streptavidin). Lanes 1 and 3: 1 μg sperm proteins (particulate fraction) that did not bind ZP. Lanes 2 and 4: ZP-bound proteins (from 1 μg ZP incubated with detergent-solubilized material from 60 μg sperm membrane proteins). Lanes 1 and 2: disulfide bonds not reduced. Lanes 3 and 4: disulfide bonds reduced. Note that 60 times the amount of sperm biotinylated proteins shown in lanes 1 and 3 were used to obtain the ZP-binding proteins shown in lanes 2 and 4.

The zona pellucida is an extracellular matrix surrounding the mammalian egg where species-specific gamete recognition and signaling occur. Pig zona pellucida were isolated in large amounts and used as an affinity matrix for detergent-solubilized, biotinylated membrane proteins of pig spermatozoa. On non-reducing SDS-polyacrylamide gel electrophoresis, specifically bound sperm proteins migrated with Mr 170,000, 150,000, 130,000, 56,000, and 50,000 (p50). Disulfide bond reduction separated each of the Mr 130–170,000 proteins into Mr 105,000 (p105) and Mr 45,000 (p45) subunits, indicating that these high Mr proteins are related. Based on two-dimensional electrophoresis, the Mr 56,000 band was composed of 3–4 proteins that migrated with Mr 56–62,000 (p56–62) in the second (reducing) dimension. p50 bound to heterologous zona pellucida (murine, bovine) and to *Xenopus laevis* oocyte envelopes, demonstrating a lack of species-specificity to its binding, and was identified as proacrosin/acrosin based on amino acid sequences of two tryptic peptides and its interaction with monospecific antibodies to proacrosin. In contrast, p105/p45 and one or more of the p56–62 proteins bound to pig zona pellucida but not to the egg extracellular matrices of the other species; these proteins therefore exhibited the species-specific binding to the zona pellucida expected for molecules involved in specific gamete adhesion. Amino acid sequences of nine tryptic peptides derived from p105/p45 did not match peptide sequences in existing databases, establishing it as a unique protein.

Degenerate oligonucleotide primers designed from tryptic peptide sequences of p105/45 were used to amplify a PCR product that encoded part of the protein; this PCR product was subsequently used as a probe to clone overlapping cDNAs that represent the entire coding sequence of the p105/45 mRNA. The 7785 base composite sequence contained a 7431 bp open reading frame; the sequences of eight tryptic peptides from p105 and five tryptic peptides from p45 were present in the 2476 amino acid deduced sequence, confirming that the open reading from encoded p105/45. The deduced sequence predicted a 2418 residue N-terminal extracellular region, a single transmembrane domain, and a 37 residue C-terminal intracellular segment. Dot matrix analysis identified four similar extracellular domains of approximately 400 residues each, and part of a fifth such domain.

Surprisingly, database comparisons revealed that the p105/45 domains are homologous to the D-domains of von Willebrand factor. The putative extracellular sequence also contained a region consisting of 53 imperfect repeats of a 7 residue sequence rich in proline and threonine residues that is characteristic of mucins. Northern blots and in situ hybridization detected expression of the p105/45 message only in spermatids. Thus, p105/45 is a sperm membrane specific protein that binds to the ZP and has structural characteristics similar to two different classes of molecules that regulate cellular interactions; these properties indicate a function for p105/45 in sperm adhesion to the zona pellucida.

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLE I

Purification and Characterization of Species Specific Egg-Binding Proteins From Sperm A. Materials and Methods 1. Protein Assay Protein concentrations were measured with bicinchoninic acid (Pierce chemical Co.), using bovine serum albumin as a standard (Smith et al., 1985).

2. Electrophoresis

Polyacrylamide gel electrophoresis (PAGE; 8% polyacrylamide gels) in the presence of SDS was performed according to Laemmli (Laemmli, 1970). Disulfide bonds were reduced by heating (95° C., 5 min) in electrophoresis sample buffer containing 20 mM dithiothreitol. Two-dimensional SDS-PAGE was performed by loading extruded 1.5 mm tube gels of non-reduced samples horizontally on the top of 1.5 mm slab gels for electrophoresis under reducing conditions. In the second dimension, proteins were reduced during stacking by overlaying the tube gel with 1% (w/v) melted agarose in 1× stacking gel buffer containing 2% (w/v) SDS and 50 mM dithiothreitol prior to electrophoresis.

Western blots

Proteins separated by SDS-PAGE were transferred to nitrocellulose membranes (Sartorius, Hayward, Calif.) by Western blotting (6 V/cm, 2 h, 22° C.) (Towbin et al., 1979). Biotinylated proteins were detected by incubating (15 min, 22° C.) the nitrocellulose sheets containing the transferred proteins (blots) with horseradish peroxidase-conjugated streptavidin (TAGO Immunologicals, Burlingame, Calif.) diluted 10,000-fold in TBST (10 mM Tris.HCl pH 7.5, 150 mM NaCl, 0.1% Tween 20); after washing with TBST (2×10 s, 2×15 min, 22° C.), peroxidase activity was detected by enhanced chemiluminescence (Amersham, Arlington Heights, Ill.). Proacrosin was detected with a monospecific antiserum to proacrosin (Hardy et al., 1987). Blots were incubated at least 1 h at 22° C. in antiserum diluted 1000-fold in TBST. After washing with TBST as for biotin detection, blots were incubated 1 h at 22° C. with horseradish peroxidase-conjugated antibody to rabbit immunoglobulin (TAGO Immunologicals) diluted 10,000-fold in TBST. Blots were then washed and developed as for biotin detection.

Preparation of zona pellucida and *Xenopus oocvte* envelopes

Porcine oocytes were isolated from sliced ovaries by step-wise sieving through screens (Dunbar et al., 1980). Up to 10 l of ovaries were used per preparation. Bovine oocytes were also isolated by sieving; up to 200 ovaries were sliced with a hand-held tool fixed with one set of ganged razor blades. Porcine and bovine ZP were isolated from oocytes by homogenization in detergent and ultracentrifugation through Percoll as for isolation of mouse ZP (see below).

Mouse ZP were isolated from freshly dissected mouse (HSD.ICR strain, 21–28 d old, Harlan-Sprague Dawley, Indianapolis, Ind.) ovaries (Bleil & Wassarman, 1986). After homogenization in buffer containing 1% (v/v) NP-40, and addition of sodium deoxycholate to 1% (w/v), ovary homogenates were mixed with isotonic Percoll (Pharmacia, Piscataway, N.J.) to produce a 50% (v/v) Percoll suspension and ultracentrifuged for 40 min at 90,000 g (35,000 rpm, Beckman 70.1 Ti rotor, 2° C.). A single, sharp ZP band was recovered at approximately 50% of the total distance of the resultant Percoll gradient. Purified ZP were washed at least 1000-fold with 1% (w/v) CHAPS in buffer HNE (20 mM NaHEPES, 130 mM NaCl, 1 mM EDTA pH 7.5) by centrifugation (2500 g, 10 min, 2° C.), resuspended in 1% CHAPS/HNE at 1–4 mg protein/ml, and stored frozen at −20° C.

By phase contrast microscopy, all ZP preparations appeared to contain only ZP fragments, and fewer than one in ten of the fragments contained adherent granular material derived from the egg cytoplasm.

Oocyte envelopes (OE) were isolated from ovaries of adult *Xenopus laevis* (Hedrick & Hardy, 1991), then washed with 1% CHAPS/HNE and stored frozen at −20° C. as for ZP isolation.

Isolation of pig sperm membranes

Spermatozoa were flushed (retrograde) from caudal epididymides of mature boars (up to 20 tissues per preparation) with a HEPES-buffered capacitation medium containing 10 $\mu$g/ml heparin (Florman et al., 1989), and capacitated at 39° C. for 4 h (Florman & First, 1988). The cell suspension was then centrifuged (1000 g, 20 min, 2° C.), and the sperm pellets were frozen on dry ice and stored at −20° C.

Frozen sperm pellets were thawed on ice in 600 ml HE/DFP (50 mM NaHEPES, 1 mM NaEDTA, 1 mM DFP pH 7.5, 0° C.). The cell suspension was filtered through a 210 $\mu$m nylon screen and equilibrated to 650 psi N$_2$ (30 min, 0° C.) in a Parr bomb. The cells were then disrupted by cavitation (Gillis et al., 1978), centrifuged (4000 g, 10 min, 2° C.), and the supernatant solution containing crude membranes was centrifuged again (235,000 g, 40 min, 2° C., Beckman Ti 45 rotor). The membrane pellets were resuspended by homogenization in 30 ml fresh HE/DFP (15 ml Dounce, tight pestle, on ice), and the membranes were washed once by dilution with 100 ml HE/DFP and ultracentrifugation (235,000 g, 40 min, 2° C.). The washed pellets were then resuspended at 20 mg protein/ml in fresh HE/DFP by Dounce homogenization. This particulate fraction was either biotinylated immediately or frozen and stored at −20° C. Using this method, a cumulative yield of 1360 mg membrane protein was obtained from 518 g of pig spermatozoa (5 preparations).

In some preliminary studies, the crude membranes were further purified by fractionation on sucrose step gradients [10, 20, 30, 40% (w/v) in HE/DFP]; however, results obtained with these purified membrane fractions were similar to those obtained with the crude particulate fraction, so further purification of the membranes was not routine.

Biotinylation and membrane protein solubilization

Amino groups of sperm membrane proteins were biotinylated with the 2-sulfo-N-hydroxysuccinimidyl ester of 6-N-caproylbiotinamide (NHS-LC-biotin, Pierce Chemical Co., Rockford, Ill.). Routinely, 40 $\mu$l of NHS-LC-biotin stock solution (50 mM in H$_2$O, prepared fresh) were added per ml of membrane suspension (20 mg protein/ml in HE/DFP) to produce a ratio of approximately 1 mol NHS-LC-biotin per 100 mol protein amino acid. After rocking for 1 h at 22° C., 20 $\mu$l 1M TrisHCl pH 8.0 were added per ml of membrane suspension, and the mixture was rocked an additional 10 min at 22° C. to quench the biotinylation reaction. The biotinylated membranes were then diluted 3-fold with fresh HE/DFP and centrifuged 25 min, 277,000 g at 2° C. (Beckman 70.1 Ti rotor) for preparative scale studies, or 15 min, 540,000 g at 2° C. (Beckman TLA 100.3 rotor) for analytical scale studies. The biotinylated membranes were then resuspended at 20 mg protein/ml in HE/DFP by dounce homogenization, on ice.

Biotinylated membranes were solubilized by adding an equal volume of 2% (w/v) CHAPS in 300 mM NaCl containing 100 $\mu$M aprotinin, 20 $\mu$M E-64, and 2 mM EDTA. After rocking for 10 min at 22° C., the membrane/detergent mixture was centrifuged as after biotinylation, and the clear supernatant solution (=detergent solubilized, biotinylated membrane protein fraction) was used for all binding studies. The SDS-PAGE patterns of the biotinylated sperm proteins obtained were identical whether proteins were detected directly (by Coomassie blue or silver staining the gels) or by detecting biotin after western blotting (by enhanced chemiluminescence). Thus, the procedure appeared to result in uniform biotinylation of the proteins in the sperm particulate fractions.

Identification and isolation of ZP-binding proteins

Unless otherwise noted, ZP-binding reactions were at 22° C. with continuous mixing using 40 $\mu$l of detergent-solubilized membranes (from 20 $\mu$g membrane protein) per 1 $\mu$g particulate ZP protein. Purified ZP in 1% CHAPS/HNE were centrifuged (2500 g, 5 min, 4° C. for preparative studies; 15,000 g, 1 min, 22° C. for analytical studies) to remove excess buffer. Solubilized, biotinylated membrane protein was then mixed with the ZP pellets, and the resultant suspension was rocked for 1 h at 22° C. Analytical scale reactions (100 $\mu$g ZP protein) were washed 320,000-fold either quickly at 22° C. with 5×200 $\mu$l wash buffer (1% CHAPS/HNE) on a manifold equipped with a 96 well 0.45 $\mu$m hydrophilic membrane filtration plate (Millipore, Bedford, Md.), or at 2° C. with 5×500 $\mu$l wash buffer by centrifugation (15,000 g, 30 s). The washed ZP with bound, biotinylated proteins from sperm membranes were then solubilized in 40 $\mu$l 1X SDS-PAGE sample buffer (no reducing agent). Preparative scale reactions (up to 10 mg ZP protein) were washed at 2° C. with 4×10 ml wash buffer (160,000-fold wash) by centrifugation (2500 g, 5 min). The ZP pellets with bound sperm proteins were then washed once quickly with 5 ml H$_2$O (0° C.) by centrifugation (2500 g, 5 min, 2° C.). In some studies, the resultant pellet was dissolved by adding an equal volume of 0.2% (w/v) SDS, and incubating at 22° C. for 45 min. Alternatively, the ZP pellet was washed again by adding an equal volume of 2×-concentrated mRIPA [10 mM NaHEPES pH 7.5, 1M NaCl, 2% (v/v) NP-40, 1% (w/v) NaDeoxycholate, 0.2% (w/v) SDS], rocking for 30 min at 22° C., and then microfuging (2 min, 14,000 g, 22° C.). Following three more equal volume washes with 1× mRIPA, the mRIPA washes containing eluted sperm proteins were pooled and stored frozen at −20° C. The mRIPA-washed ZP pellet was washed twice more with H₂O by microfugation as for mRIPA, dissolved in SDS as described above, and stored frozen at −20° C.

Biotinylated sperm proteins that had bound to the ZP were separated from solubilized ZP glycoprotein by affinity chromatography on streptavidin-agarose (Pierce Chemical Co., Rockford, Ill.). Stock solutions of NaCl, NaDeoxycholate, and NP-40 were added to SDS-solubilized ZP/binding proteins to produce 1× mRIPA concentrations, and the solution (containing up to 23 mg ZP protein) was applied to a streptavidin-agarose column (0.5 ml bed volume, equilibrated in mRIPA). The column was washed with 20 bed volumes of mRIPA and 10 bed volumes of H₂O. The column bed containing bound, biotinylated proteins was then collected in 0.5 ml elution buffer [4% (w/v), 2 mM D-biotin, 125 mM TrisHCl pH 6.8] and the suspension heated (95° C., 20 min). The suspension was then poured back into the empty column and washed with 1×0.5 ml 6M urea containing 1 mM D-biotin and then with 3×0.5 ml H₂O to collect the eluted, biotinylated sperm proteins.

Peptide mapping and amino acid sequencing

Biotinylated ZP-binding proteins purified by streptavidin-agarose chromatography were separated by SDS-PAGE, blotted to polyvinylidene difluoride membranes, and proteolyzed in situ with trypsin (Fernandez et al., 1992). Tryptic peptides released from the membrane were purified by sequential reversed-phase HPLC separations with two different solvent systems (Fernandez et al., 1992; Krupinski et al., 1989). The twice-purified peptides were then sequenced by automated Edman degradation using Applied Biosystems model 475A or 477A sequenators (Krupinski et al., 1989).

B. Results

Results of a typical ZP-binding study are shown in FIG. 1. Biotinylated proteins of Mr 170,000, 150,000, 130,000, 72,000, 56,000 and 50,000 bound to the ZP as assessed by non-reducing SDS-PAGE. The proteins that bound to the ZP were not major sperm biotinylated proteins, suggesting specificity to their interaction. However, the amount of the 72,000 Mr protein that bound to the ZP at physiological salt concentrations was highly variable, and decreased dramatically at ionic strengths above 150 mM, suggesting that this protein bound primarily by ionic interactions that may not be specific. In contrast, the other proteins consistently bound to the ZP even at high ionic strength. Disulfide bond reduction altered the migration of the sperm proteins (FIG. 1); under reducing conditions, 105,000, 78,000, 56,000, 50,000, and 45,000 Mr bands were observed.

Figure 2A:
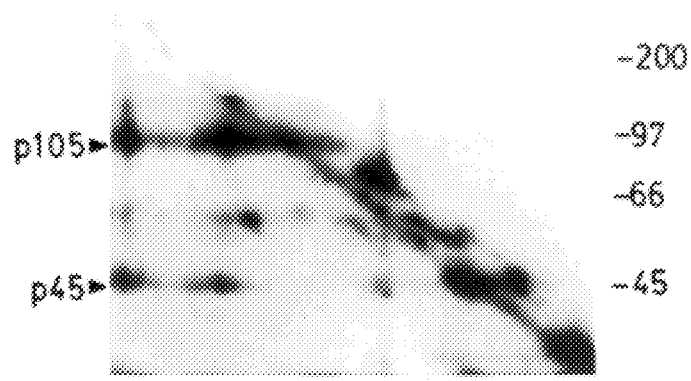
FIGS. 2A, 2B and 2C.
Figure 2B:
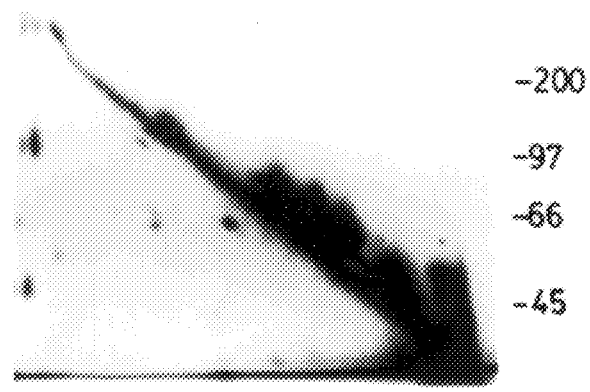
Figure 2C:
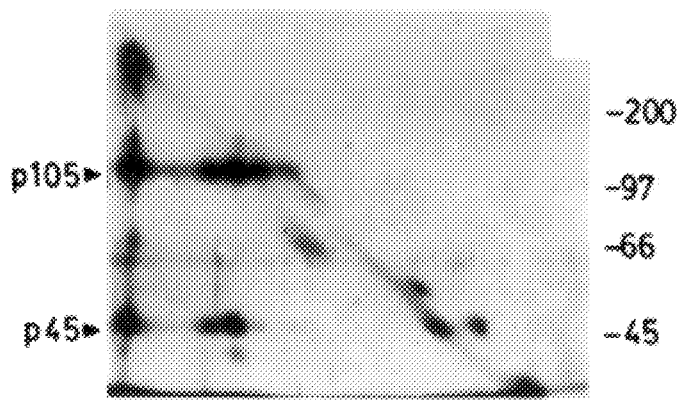

The differences in the electrophoretic patterns obtained under reducing and non-reducing conditions suggested that the ZP-binding proteins possessed intra- and intermolecular disulfide bonds. To characterize further these disulfide bonds, ZP-bound proteins were separated by two-dimensional SDS-PAGE (disulfide bonds not reduced in the first dimension, reduced in the second dimension), then detected on Western blots (FIG. 2). The two-dimensional SDS-PAGE pattern of the ZP-bound fraction (FIG. 2A) differed markedly from the patterns observed for the starting material in the binding study and for the ZP non-binding fraction (FIG. 2B). The Mr 130,000, 150,000, and 170,000 proteins migrated as Mr 105,000 (p105) and Mr 45,000 (p45) subunits after reduction (FIGS. 2A & 2C). Thus the Mr 130–170,000 proteins are related, each being comprised in part of p105 and p45, and they will be referred to collectively as p105/45. Some of the very high Mr material that migrated near the top and at the stacking/resolving interface of the first dimension also contained p105 and p45 (FIGS. 2A & 2C), and could represent covalent oligomers of p105/45. Reduction decreased the mobility of the Mr 72,000 protein, but did not change the mobility of the Mr 50,000 protein (p50). In addition, 3 or 4 biotinylated proteins that comprised the Mr 56,000 band were resolved (Mr 56,000–62,000 under reducing conditions). These proteins will be referred to collectively as p56–62. The results are summarized in Table 1.

TABLE 1

Summary of characteristics of ZP-binding proteins

| $M_r$ | | Protein | Species |
|---|---|---|---|
| Not reduced | Reduced | designation | specificity |
| i >>200,000 | 105,000 | p105/45 | + |
|  | 45,000 |  |  |
| 130,000–170,000 | 105,000 | p105/45 | + |
|  | 45,000 |  |  |
| 72,000 | 78,000 |  | − |
| 56,000 | 56,000–62,000 | p56-62 | ± |
| 50,000 | 50,000 | p50 | − |

Figure 3:
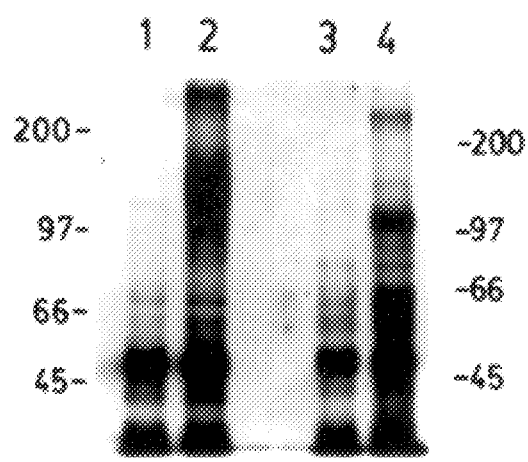
FIG. 3. Binding of pig sperm proteins to mouse or pig ZP. Shown are SDS-PAGE/Western blots of sperm biotinylated proteins (detected with horseradish peroxidase-conjugated streptavidin). Lanes 1 and 3: pig sperm proteins that bound to mouse ZP. Lanes 2 and 4: pig sperm proteins that bound to pig ZP. All lanes: ZP-bound proteins (from 1.25 μg ZP incubated with detergent-solubilized material from 80 μsperm membrane proteins) remaining after washing with 1% CHAPS/HNE. Lanes 1 and 2: disulfide bonds not reduced. Lanes 3 and 4: disulfide bonds reduced.
Figure 4A:
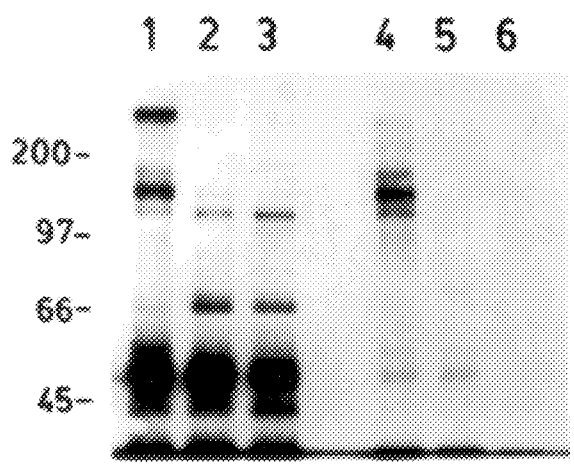
FIG. 4.
Figure 4B:
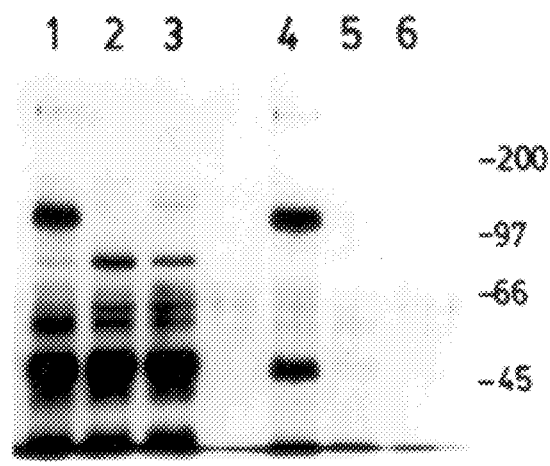

As the sperm proteins that bound reproducibly to the ZP at physiological ionic strength were minor proteins relative to those that did not bind, specificity of binding was evident, but species-selective binding would more strongly suggest that the bound proteins were of physiological importance. Although p50 in 1% CHAPS/HNE bound to both pig ZP and mouse ZP, p105/45 and one or more of the p56–62 proteins did not bind to the mouse ZP under these or other conditions tested (FIG. 3). Similar results also were obtained using bovine ZP and egg envelopes isolated from *Xenopus laevis* oocytes; in 1% CHAPS/HNE, p50 appeared to bind equally well to pig ZP, bovine ZP, and Xenopus envelopes, but one or more of the p56–62 proteins bound primarily and p105/45 bound exclusively to the pig ZP (FIG. 4). When these egg investments with bound pig sperm proteins were subsequently washed with a stronger combination of detergents and ionic strength (mRIPA) to examine relative binding affinities, the species specificity of p105/45 binding to the ZP was particularly evident (FIGS. 4 and 2C). Under these conditions, p50 and most or all of the p56 proteins were eluted from the pig ZP. Essentially no pig sperm proteins remained bound to mRIPA-washed bovine ZP or Xenopus envelopes. In contrast, p105/45 bound to the pig ZP with remarkably high apparent affinity, since it remained quantitatively bound to the pig ZP even after extensive washing with buffers containing high concentrations of detergent and NaCl (FIG. 4, lane 4).

Figure 5:
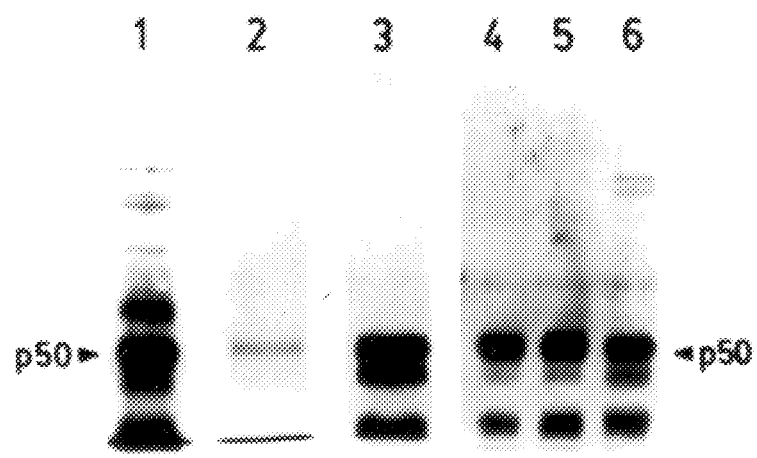
FIG. 5. Purification and characterization of p50. Lane 1: Western blot, biotinylated proteins detected with horseradish peroxidase-streptavidin, of pig sperm proteins that had bound to 2.5 μg pig ZP and were then eluted from ZP with mRIPA. Lane 2: Coomassie blue stained SDS-PAGE of p50 that had bound to pig ZP and was then eluted from the ZP with mRIPA and purified by streptavidin-agarose chromatography. Lanes 3–6: Western blots, proacrosin detected with a monospecific heteroantiserum. Lane 3: proteins that had bound to 10 μg pig ZP and were then eluted from the ZP with mRIPA. Lanes 4–6: Same samples as Lanes 1–3 of FIG. 4. All lanes: disulfide bonds reduced.

To purify ZP-binding proteins for amino acid sequencing, the inventors performed large scale ZP-binding reactions using pig ZP and 1% CHAPS-solubilized, biotinylated proteins from pig sperm particulate fractions; the ZP with bound sperm proteins were washed extensively with 1% CHAPS/HNE in a manner similar to the analytical scale studies. Since the p45 subunit of p105/45 could not be resolved from p50 in one-dimensional SDS-PAGE, the inventors washed the ZP (and associated sperm proteins) with mRIPA to remove p50 (FIG. 5); p50, p105, and p45 were then purified by chromatography on streptavidin-agarose, and tryptic peptides isolated from the purified proteins were sequenced. The sequences of two p50 peptides were found to match residues 100–112 and 123–132 of the porcine proacrosin sequence (Baba et al., 1989). On immuno blots, p50 that had bound to pig ZP reacted strongly with a monospecific antibody to proacrosin (FIG. 5), as did p50 that bound to bovine ZP or Xenopus envelopes. Thus p50 is proacrosin/acrosin. Two other processed forms of proacrosin also were recognized by the proacrosin antibody (FIG. 5).

Sequences of seven p105 peptides and two p45 peptides were also obtained and compared with the sequences in the PIR 37 and Swiss-Prot 26 databases. No significant matches with known sequences were found.

C. Discussion

By using the extracellular matrix of the porcine egg as an affinity matrix, the inventors have isolated sperm proteins that are involved in species-specific gamete adhesion and/or signaling. The approach used has the advantage of isolating sperm molecules that interact with the zona pellucida of the egg without prior knowledge of the potential functions of any protein. Various evidence suggests that the binding of the sperm proteins was specific. First, only minor sperm proteins bound to the ZP under the described conditions, indicating that the observed binding was not adventitious binding that could occur with major proteins of the sperm membrane. Second, the apparent affinities of binding were very high, since the proteins remained bound even after extensive washing by centrifugation. And third, the p105/45 and p56–62 classes of protein bound in a species specific manner to the ZP. Although the use of high apparent affinity as a criterion may exclude important regulatory proteins that bind less avidly than p105/45 or p56–62, the method provides a novel means to assess the molecular basis of gamete recognition and signaling at the sperm surface.

Since acrosome-intact spermatozoa adhere preferentially to the ZP surrounding conspecific eggs in vitro (Yanagimachi, 1981; Peterson et al., 1980; Schmell & Gulyas, 1980), and the limited amount of information available indicates that induction of the acrosome reaction by the ZP is at least species selective (Cherr et al., 1986; Moller et al., 1990; Uto et al., 1988), species-specificity of sperm protein binding to the ZP appears to be one of the most important criteria for functional relevance. The species-specific binding of p105/45 and of one or more of the p56–62 proteins indicates that these proteins mediate, at least in part, the species-specific adhesion of spermatozoa to the ZP, and possibly transduction of the signal for the acrosome reaction as well.

Sperm proteins that may recognize the egg extracellular matrix have been identified previously using a number of different methods. For example, solubilized, labeled (biotin or $^{125}$I) ZP bound to proacrosin/acrosin that is purified by reversed-phase HPLC or separated by SDS-PAGE and transferred to nitrocellulose blots (Jones & Brown, 1987; Topfer-Peterson & Henschen, 1987; Urch & Patel, 1991). Although small differences in the binding of homologous and heterologous ZP to proacrosin/acrosin (on blots) were observed (Williams & Jones, 1993), species-specificity was generally not apparent. Since pig proacrosin/acrosin bound to all egg investments tested in these studies, the inventors conclude that the ZP-binding activity of this protein alone does not account for species-specific adhesion of spermatozoa to the ZP.

Several small (10–20,000 Mr) proteins of pig spermatozoa have been identified on western blots probed with $^{125}$I-labeled, solubilized ZP (O'Rand et al., 1985; Jonakova et al., 1991; Parry et al., 1992). At least some of these proteins are present in accessory gland secretions and on spermatozoa in high concentrations (O'Rand et al., 1985; Jonakova et al., 1991; Parry et al., 1992) suggesting that they bind the ZP with low affinity. These proteins, if present, would have migrated at the dye front of our gels and would not have been detected.

A 95,000 Mr apparent ZP-binding protein has also been identified on western blots of mouse sperm proteins probed with $^{125}$I-labeled, solubilized ZP (Leyton & Saling, 1989). Evaluating the specificity of binding observed with this method is difficult, since specificity would depend on the concentrations of ZP and sperm proteins used and the extent to which native structure of these proteins was retained or recovered. Nevertheless, this technique is effective in some receptor-ligand systems. The method the inventors used for identification of ZP-binding proteins avoids denaturation of ZP or sperm proteins prior to their interaction. The fact that the inventors did not observe a 95,000 Mr ZP-binding protein suggests that prior denaturation of sperm proteins, ZP, or both is necessary for association of this protein with ZP glycoproteins. Denaturation may also explain why some of the ZP-binding proteins the inventors identified were not detected in previous studies.

A function for galactosyl transferase in mouse sperm adhesion to the ZP has been extensively characterized using a variety of methods (Shur, 1989; Miller et al., 1992). Mouse sperm surface galactosyl transferase is a 60,000 Mr plasma membrane-associated variant, encoded by an alternate transcript, of the enzyme that is expressed in the Golgi of other tissues (Lopez et al., 1991; Shur & Neely, 1988). A 56,000 Mr protein on the surface of mouse spermatozoa, designated sp56, has been identified by photoaffinity cross-linking using solubilized, $^{125}$I-labeled ZP3 as the ligand (Bleil & Wassarman, 1990). A sperm membrane protein designated PH-20 that exists as 64,000 and 56,000 Mr isoforms has been identified with a monoclonal antibody that inhibits adhesion of guinea pig spermatozoa to the ZP (Primakoff et al., 1985; Primakoff et al., 1988). Species-specificity of galactosyl transferase, sp56, or PH-20 binding to the ZP has not been reported.

The inventors conclude that two distinct classes of sperm membrane proteins (p105/45 and p56–62) may mediate species-specific adhesion of pig spermatozoa to the egg extracellular matrix. These studies are the first to use apparent high affinity binding to intact ZP and species-selectivity as criteria for specificity, and the first to identify a ZP-binding protein with the characteristics of p105/45.

EXAMPLE II

Cloning and Sequencing of p105/45

A. Materials and Methods 1. p105/45 purification and peptide sequencing p105/45 was purified by large scale binding of detergent-solubilized, biotinylated sperm membrane proteins to native porcine zona pellucida, with subsequent separation of bound, biotinylated proteins from zona pellucida by streptavidin-agarose chromatography (Example I). SDS-PAGE, peptide mapping and sequencing, western blots, and detection of biotinylated proteins with peroxidase-conjugated streptavidin and enhanced chemiluminescence were also as described in Example I.

2. RNA isolation

Total RNA was isolated by homogenizing tissues in guanidinium thiocyanate and N-lauroyl sarcosine, extracting with acidic phenol/CHCl$_3$, and precipitating with isopropanol (Chomczynski & Sacchi, 1987). Poly(A)+RNA was isolated from total RNA by oligo(dT)-cellulose chromatography (Fast Track Kit, Invitrogen). RNAs larger than 5 kb in length were purified from total RNA by gen filtration on Sephacryl S-1000.

3. Polymerase chain reaction (PCR)

PCR with degenerate oligonucleotide primers (Midland Certified Reagent Co.) was performed in 100 μl volumes containing 53 ng template DNA, 0.5 μM each primer, 200 μM each dNTP, and 5 U Taq polymerase in buffer (10 mM Tris-Cl pH 8.3, 1.5 mM MgCl$_2$, 50 mM KCl 0.01% gelatin). Amplifications were for 40 cycles (denature 94° C. 1 min, anneal 50° C. 2 min, extend 72° C. 3 min) using a conventional thermal cycler (Ericomp). Sequences of degenerate primers were:
GAATTCGAATTCGA(A/G)GGICA(A/G)CCICCIGCITT(C/T)TA(C/T)(C/T)T (sense, SEQ ID NO:3) and GGATCCGGATCCCAIGCIGGIGC(C/T)TG(A/G)AAIGCIGC(C/T)TG (antisense, SEQ ID NO:4). PCR with specific oligonucleotide primers (5' RACE, see below) was performed in glass capillaries (10 μl reaction volume) using air-driven thermal cycler (Idaho Technologies). Amplifications were for 35 cycles (denature 94° C. 0 s, anneal 60° C. 0 s, extend 72° C. 30 s) with 0.5 μM each primer, 200 μM each dNTP, and 2.5 U Taq polymerase in buffer (50 mM Tris-Cl pH 8.3, 2.0 mM MgCl$_2$, 0.25 mg/ml BSA, 1 mM tartrazine, 0.5% ficoll).

4. cDNA library construction and screening cDNA libraries were prepared from pig testis poly(A)$^+$ RNA by priming first strand synthesis with either oligo-dT or random hexamers. Double-stranded cDNA with EcoRI sticky ends was prepared using the Superscript Choice kit (Bethesda Research Laboratories) and ligated into EcoRI-cut, dephosphorylated λZAPII (Stratagene). The resultant phage DNA was packaged with Gigapack Gold II (Stratagene). All libraries were screened first as primary libraries (unamplified) by hybridizing duplicate nylon filter (Hybond N, Amersham) lifts with a single-stranded PCR product labeled by asymmetric PCR (0.5 μM antisense primer, 5 nM sense primer). Pure phage plaques were picked, eluted, and pBluescript plasmids containing cDNA inserts were rescued in SOLR cells (Stratagene). Plasmid DNA was purified by alkaline lysis mini-preps (Sambrook et al., 1989) or by Wizard mini- or midi-preps (Promega).

5. DNA sequencing and sequence analysis

Restriction fragments of pBluescript inserts were subcloned into M13mp18 and M13mp19 and sequenced manually by dideoxy chain termination (Sanger et al., 1977) using Sequenase II (U.S. Biochemicals) and $^{35}$S-dATP. Prior to ligation into vector, specific restriction fragments were purified by agarose gel electrophoresis in TAE (Sambrook et al., 1989) and QIAEX extraction (QIAGEN) of DNA in the excised bands. Sau3AI or PstI fragments were shotgun-cloned into BamHI- or PSTI-cut vector, respectively. RACE products were cloned in pBluescript and sequenced by double-stranded cycle sequencing using an Applied Biosystems automated sequencer. Both strands of cDNAs spanning the entire length of the p105/45 message were sequenced at least once, and the composite sequence was assembled and analyzed using DNASTAR software.

6. 5' RACE cDNA corresponding to the 5' end of the p105/45 message was amplified from gel filtration-purified pig testis RNA (larger than 5 kb) by 5' RACE using the 5' Amplifinder kit (Clontech). Primary 5' RACE products were excised from low melting point agarose/TAE gels and re-amplified using nested antisense primers prior to purification, restriction enzyme digestion, and cloning.

7. Northern blots

Poly(A)$^+$RNAs from pig brain, liver, heart, lung, epididymis, kidney, spleen and testis were separated on 1% agarose/formaldehyde gels and blotted overnight to nylon membranes (Sambrook et al., 1989). Blots were hybridized with a 900 bp EcoRI-XbaI fragment (from a partial length cDNA clone) that had been labeled with α$^{32}$P-dCTP by random nonamer priming (Redi-Prime, Amersham). Hybridized blots were washed at high stringency (1×10 min, 2× SSC, 0.1% SDS, 65° C., and then 2×20 min, 0.5× SSC, 0.1% SDS, 65° C.), and exposed at 85° C. to Hyperfilm-MP (Amersham).

8. In situ hybridization

Paraffin-embedded sections of pig testis (Novagen) were de-waxed and hybridized with digoxigenin-labeled RNA probes, then washed at high stringency (Vassar et al., 1993). Digoxigenin was then detected by incubation with alkaline phosphatase-conjugated antidigoxigenin followed by color development with 5-bromo-4-chloro-3-indoylphosphate and nitro blue tetrazolium (Vassar et al., 1993). Sense and antisense probes corresponding to the 1566 bp BamHI-SalI 3' end fragment of the p105/45 cDNA were synthesized with T3 or T7 polymerases using templates of appropriately linearized pBluescript plasmids containing the 1566 bp insert.

B. Results

Figure 6:
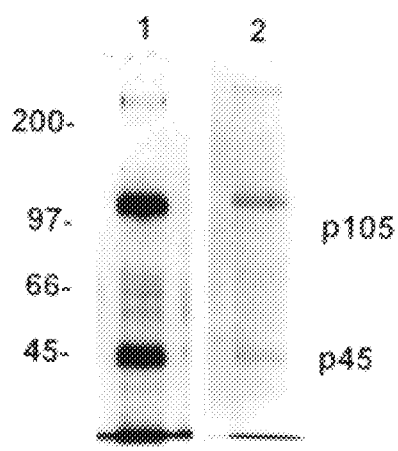
FIG. 6. Purification of p105/45. Lane 1: SDS-PAGE/western blot (disulfide bonds reduced) of biotinylated proteins from detergent-solubilized pig sperm membranes that remained bound to native porcine ZP after extensive washing (by centrifugation) consecutively with 1% CHAPS/HNE [1% (w/v) CHAPS in 20 mM NaHEPES, 130 mM NaCl, 1 mM EDTA, pH 7.5], and then with mRIPA [1% (v/v) NP-40, 0.5% sodium deoxycholate, 0.1% SDS in 25 mM NaHEPES, 0.5M NaCl, 1 mM EDTA, pH7.5]. Biotinylated proteins were detected with peroxidase-conjugated streptavidin and enhanced chemiluminescence. Lane 2: SDS-PAGE (reducing conditions, stained with Coomassie brilliant blue R-250) of p105/45 purified by large-scale binding of biotinylated sperm membrane proteins to native ZP and subsequent separation of biotinylated proteins from ZP by streptavidin-agarose chromatography.

As reported in Example I, p105/45 bound species-specifically and with very high apparent affinity to the porcine zona pellucida; this property was exploited for its purification (FIG. 6). A cumulative yield of approximately 30 μg of p105 and 10–15 μg of p45 was obtained from a total of 800 mg sperm membrane protein and 40 mg zona pellucida protein (4 preparations). Amino acid sequences of eight p105 and five p45 tryptic peptides were determined (Table 2). These peptide sequences were all unique when compared with sequences in the PIR database.

TABLE 2

Sequences of p45 and p105 tryptic peptides. X = not determinable.
Underlined residues differ from the amino acid sequence deduced from the long open reading frame of the p105/45 message.

| PROTEIN | PEPTIDE SEQUENCE | LOCATION |
|---|---|---|
| p45 | VTYILAQP | SEQ ID NO: 5 |
|  | LFV<u>Y</u>VP | SEQ ID NO: 6 |
|  | VYVTLPBSTVTLLK | 859 to 872 |
|  | VTLPMPS | 883 to 890 |
|  | XLGSS<u>Y</u>QT | SEQ ID NO: 7 |
| p105 | GGNLE<u>A</u>KYVR | SEQ ID NO: 8 |
|  | LGASWK | 1349 to 1354 |
|  | GSYHPVGESWYTDNS | 1518 to 1532 |
|  | EGQPPAFYLR | 1624 to 1633 |
|  | QVYVDIFNTLVTLKQDQVLIXGT | 1634 to 1656 |
|  | VSLPATTQIR | 1658 to 1667 |
|  | AQEQCQAAFQAPAWANCAT | 1777 to 1795 |
|  | GTFLPVGR | 1914 to 1921 |

Degenerate oligonucleotide primers were designed using the amino acid sequences of two p105 peptides (EGQPPAFYLR, position 1624 to 1633 of SEQ ID NO:2 and AQEQCQAAFQAPAWANCAT, position 1777 to 1795 of SEQ ID NO:2). The primers were used with template cDNA prepared from pig testis poly(A)$^+$RNA to amplify a 500 bp product by PCR. The 167 residue amino acid sequence deduced from the DNA sequence of the PCR product contained the sequences of two p105 peptides (QVYVDIFNTLVTLKQDQVLIXGT, position 1634 to 1656 of SEQ ID NO:2 and VSLPATTQIR, position 1658 to 1667 of SEQ ID NO:2) in addition to the two peptides used to design the degenerate primers, thus confirming that the 500 bp PCR product encoded part of p105. A preliminary northern blot of pig testis poly(A)+RNA hybridized with the $^{32}$P-labeled PCR product indicated that the full length of p105/45 message was at least 7.5 kb long.

Numerous cDNA clones were isolated from oligo-dT-primed and random hexamerprimed cDNA libraries (prepared from pig testis poly(A)+RNA) using the $^{32}$P-labeled PCR product as a probe. Two overlapping cDNA clones encompassing 6.5 kb of the p105/45 message were sequenced, but no candidate translation start site was identified. Although more than 2 million primary recombinant plaques were screened, no cDNA clone extending further 5' than these two cDNAs was isolated. The inventors therefore cloned approximately 1.3 kb more 5' end cDNA by 5' RACE. Analysis of the 7785 base composite sequence obtained revealed a 297 base 5' untranslated region, a satisfactory translation start site (Kozac, 1989), a 7431 base open reading frame, and a 57 base 3' untranslated region containing a polyadenylation signal and a poly(A) tail (FIG. 7).

Figure 9:
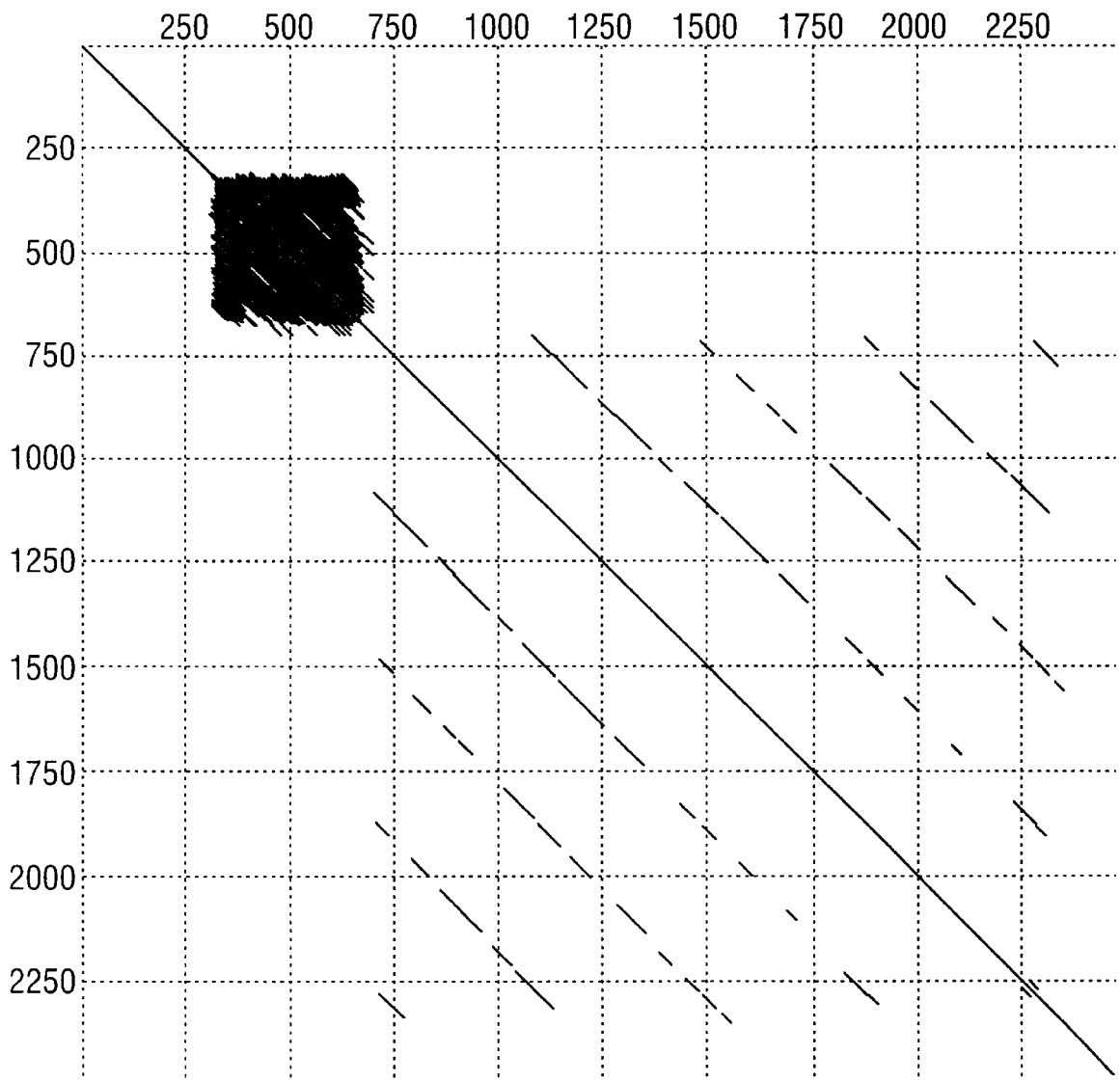
FIG. 9. Dot matrix plot of 2476 residue deduced sequence compared with itself. A highly repetitive region of the sequence is readily apparent between residues 300 and 700. Four mutually similar domains of approximately 400 residues each, and part of a fifth such domain, were also detected as indicated by the broken lines parallel to the diagonal.
Figure 10:
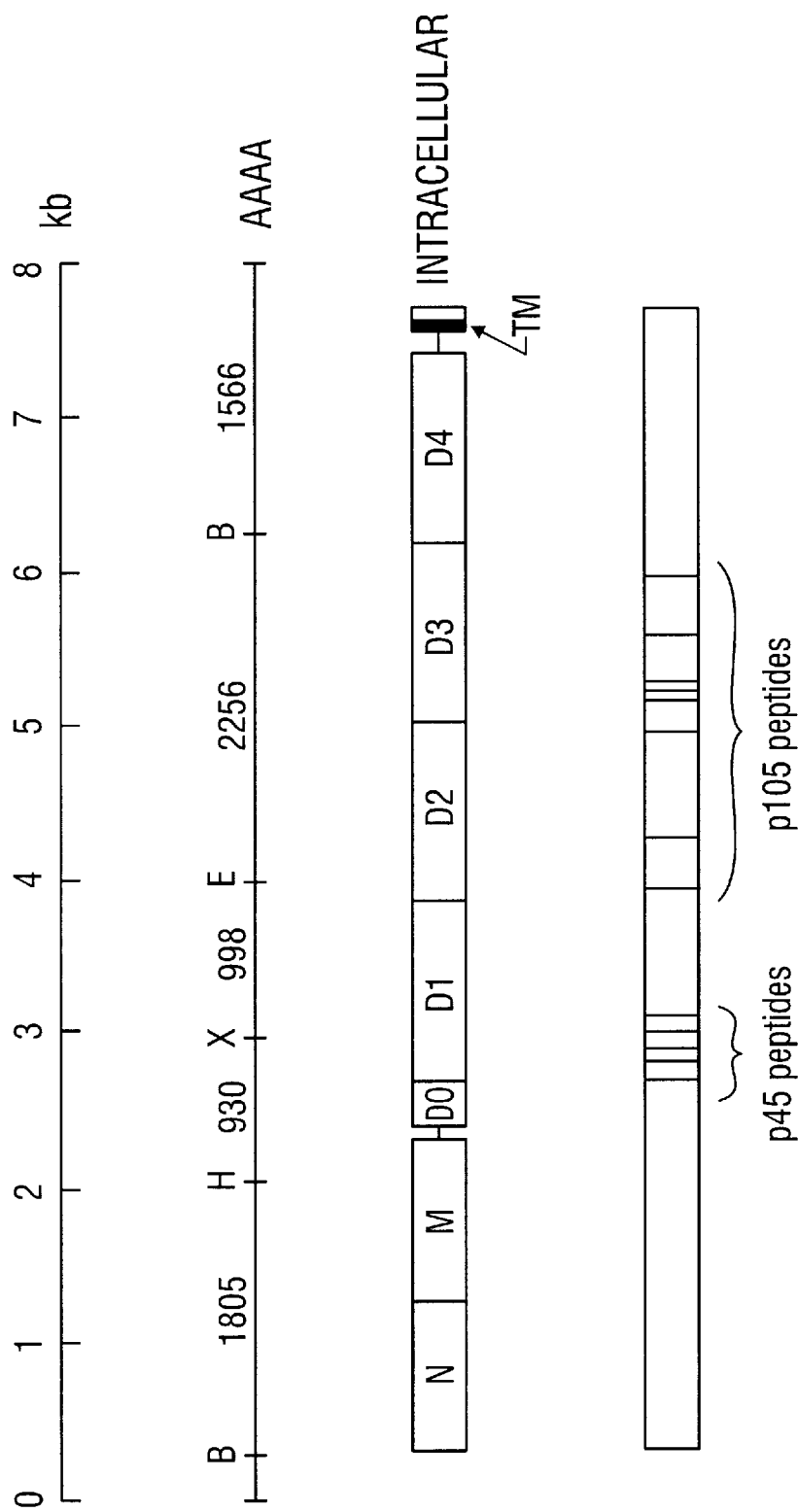
FIG. 10. Restriction map of the composite nucleotide sequence, predicted domain structure of the 2476 residue protein deduced from the long open reading frame of the p105/45 message, and locations of p105 and p45 peptide sequences within the deduced sequence.

The 2476 residue amino acid sequence deduced from the long open reading frame contained the sequences of the eight p105 and five p45 peptides (Table 2 and FIG. 8), with a few minor discrepancies that probably reflect errors in the peptide sequences. The deduced sequence predicted an N-terminal 2431 residue extracellular region, a single membrane-spanning segment and a C-terminal 37 residue intracellular segment. Dot matrix analysis of the deduced sequence is shown in FIG. 9. A region of highly repetitive sequence between residues 300 and 700 was evident. Closer examination of this sequence revealed that it consisted of 53 imperfect repeats of a seven residue sequence rich in proline and threonine (FIG. 8). Four mutually similar tandem domains of approximately 400 residues each, preceded by a partial fifth such domain, followed the mucin-like domain (FIG. 9). Conservation of cysteine residues at numerous positions within the five domains was readily apparent. Unexpectedly, sequence comparisons (PIR database) revealed that these domains are homologous to the D-domains of von Willebrand factor (vWF). A sequence of vWF D-domains has been conserved in two of the p105/45 D-domains (CGLCG, designated D1 and D2, SEQ ID NO:2, positions 933 to 937 and 1321 to 1325). In addition, the partial D-domain of p105/45 (designed D0) truncated at precisely the same point in the sequence as a truncated D-domain present in the vWF precursor. A restriction map of the composite nucleotide sequence, the predicted domain structure of the protein encoded by the open reading frame and the locations of the p105 and p45 peptide sequences within the deduced amino sequence are shown in FIG. 10. All of the p45 peptide sequences were present in the predicted D1 domain, and the p105 peptide sequences were present in the predicted D2 and D3 domains.

Figure 11:
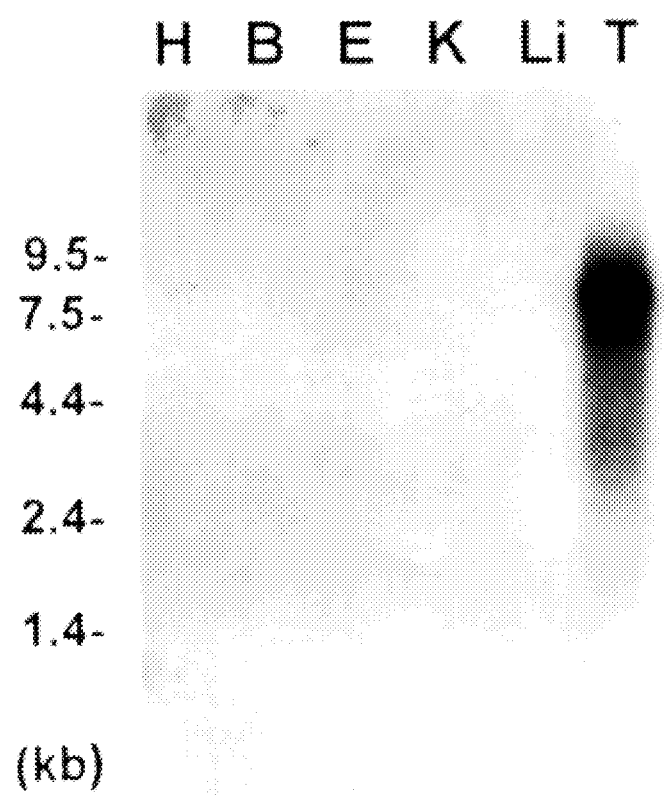
FIG. 11. Northern blot of poly(A)+RNAs isolated from pig tissues hybridized with a 900 bp $^{32}$P-labeled p105/45 specific probe. H: 4.5 μg heart RNA, B: 4.5 μg brain RNA, E: 3.4 μg epididymis RNA, K: 3.3 μg kidney RNA, Li: 2.9 μgliver RNA, T: 3.0 μg testis RNA. Migration of RNA standards (Bethesda Research Laboratories) is indicated on the left. 47 hour exposure.
Figure 12A:
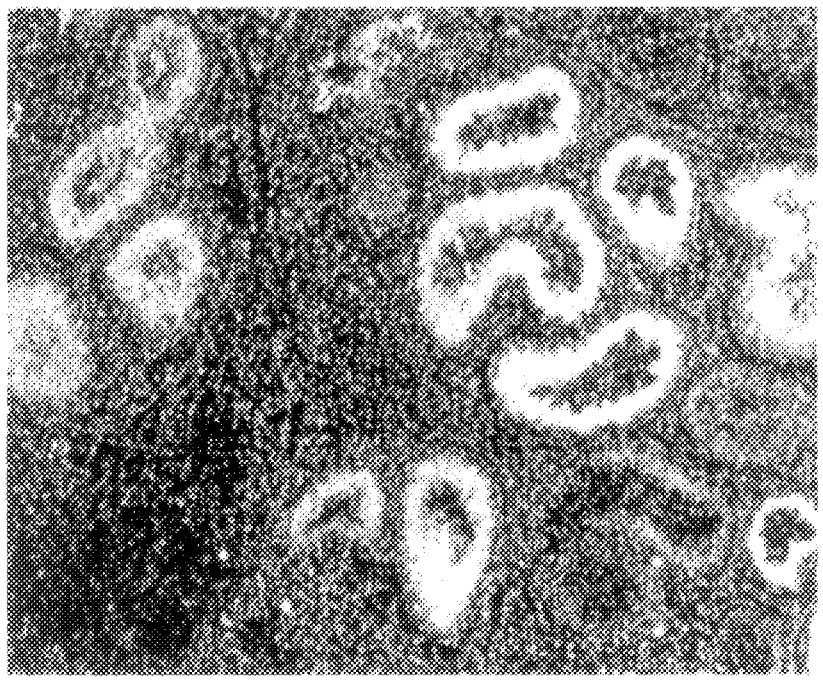
FIG. 12. Consists of Panels A through E, which represent the localization of p105/45 message expression by in situ hybridization.
Figure 12B:
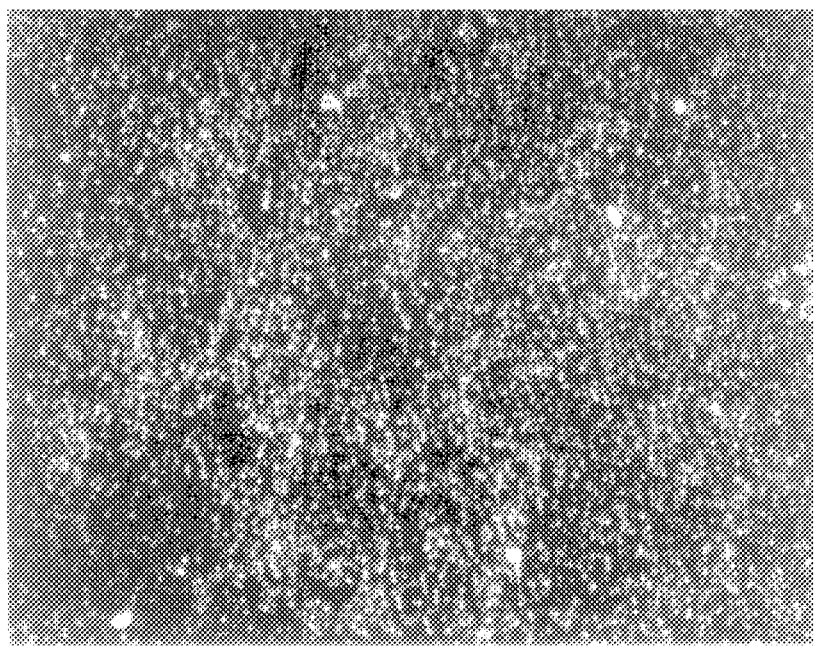
Figure 12C:
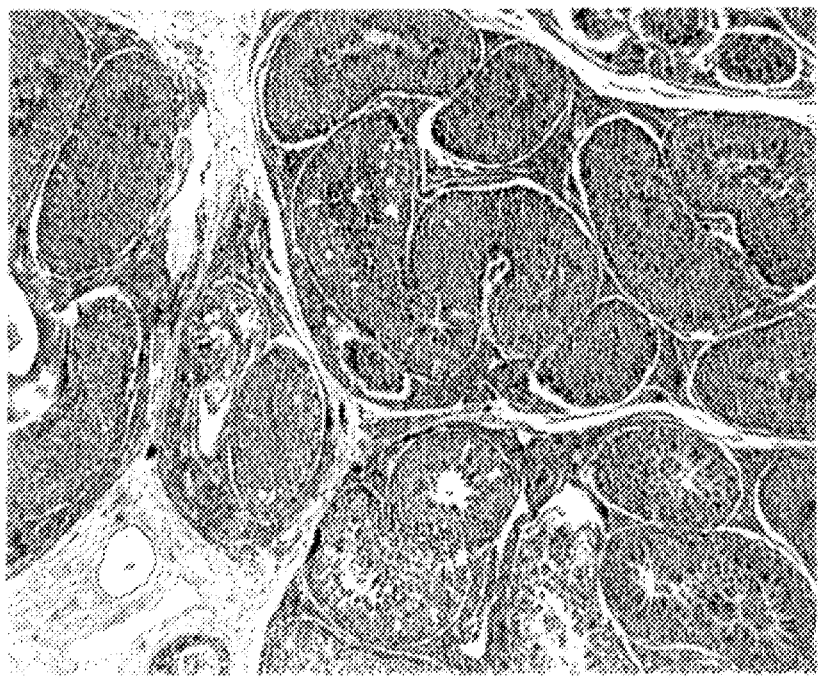
Figure 12D:
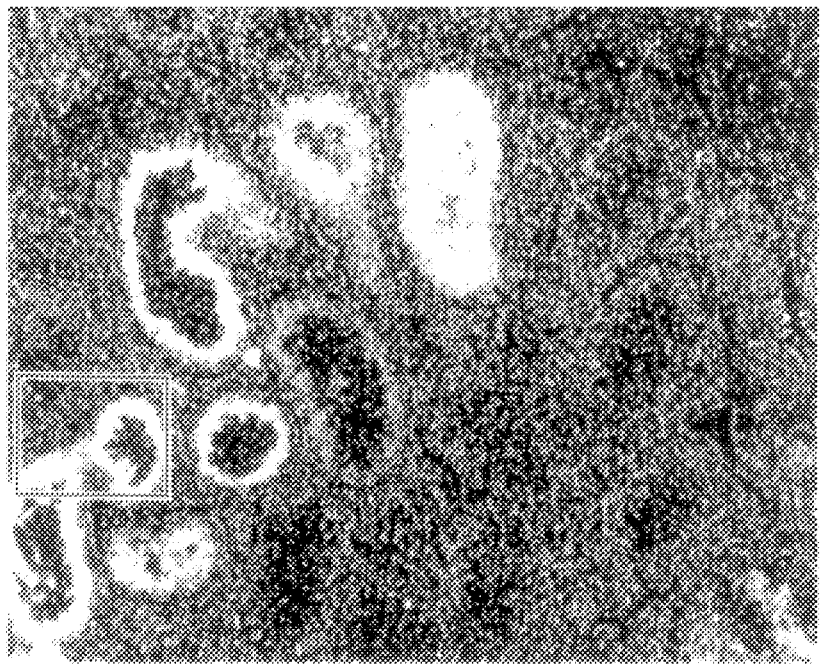
Figure 12E:
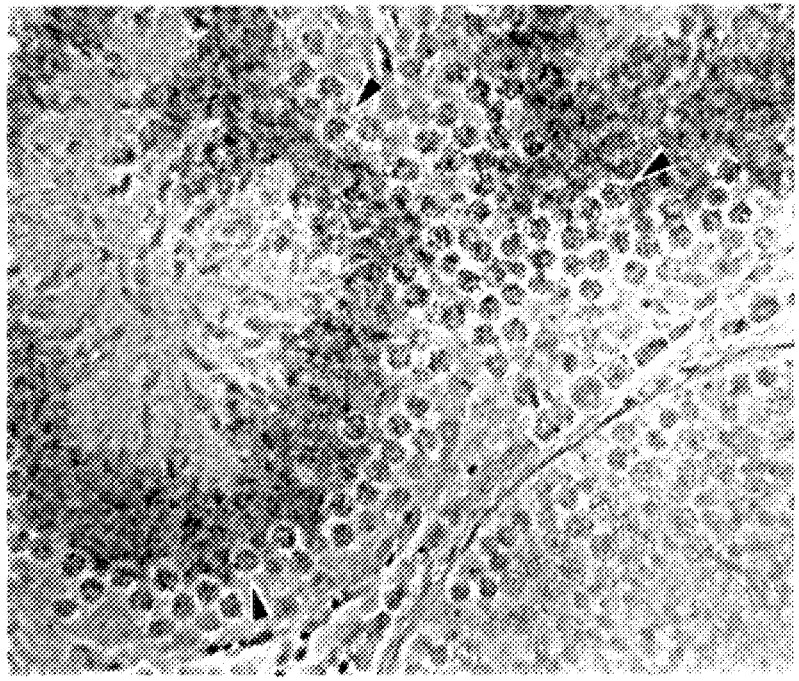

A 900 bp p105/45 probe hybridized with a 7.5–8 kb message present in poly(A)+RNA isolated from pig testis; no hybridization with poly(A)+RNAs from various other pig tissues was observed (FIG. 11). As similar amounts of poly(A)+RNAs were used, the apparent absence of expression in tissues other than testis cannot be a function of generally low synthesis of mRNAs in some tissues. The testicular cell types that express p105/45 message were identified by in situ hybridization (FIG. 12). No specific hybridization with interstitial (Leydig) cells was observed. Hybridization was restricted to the germinal epithelium of the seminiferous tubules; only a fraction of the tubules in a given section hybridized strongly with the p105/45 probe. Within strongly hybridizing tubules, expression was high only in spermatids.

C. Discussion

The inventors have purified the p105 and p45 subunits of a sperm membrane protein that bound species specifically to the porcine ZP, and cloned cDNAs encompassing the message that encodes it. The presence of eight p105 and five p45 peptide sequences in the deduced sequence confirms that the 7431 base open reading frame encodes the protein that bound species specifically to the ZP. Thus p45 and p105 are products of the same gene, and were produced by proteolysis of a larger precursor. The predicted molecular weight (270 kDa) of the protein encoded by the open reading frame is much larger than the sum (Mr 150,000) of the apparent sizes of the P105/45 subunits, indicating that a substantial amount of the mass of the p105/45 precursor had been removed proteolytically from the protein that bound to the ZP. This apparent processing may be due to physiological effects or may be a consequence of the purification procedure or a combination of these two possibilities.

Highly repetitive amino acid sequences rich in proline and threonine residues are characteristic of mucins (Hilkens et al., 1992). Thus the highly repetitive region between residues 300 and 700 of the p105/45 deduced sequence is a mucin-like domain. Mucins are heavily O-glycosylated on numerous serine and threonine residues, and their polypeptide chains have extended structures owing to the presence of many proline residues (Hilkens et al., 1992). These structural properties reflect the functions of mucins in regulating cellular interactions; the large, carbohydrate rich domains extend beyond most other cell surface glycoproteins and thereby inhibit some types of cell adhesion or promote cell adhesion by providing the carbohydrate ligands for selectins on the surfaces of other cells (Hilkens et al., 1992). It is possible that the mucin-like domain of p105/45 functions similarly during sperm transport through the female reproductive tract or during sperm-ovum interactions.

The inventors have observed high Mr sperm proteins (SDS-PAGE, non-reducing conditions) bound to the porcine ZP that appear to be covalent oligomers of p105/45 (Example I). The vicinal cysteines of the aforementioned vWF pentameric sequence may mediate covalent oligomerization of vWF monomers by disulfide interchange (Mayadas & Wagner, 1992). Hence, conservation of this motif in the D1 and D2 domains of P105/45 may reflect an important function in covalent oligomerization of p105/45. Such oligomerization could be important in sperm adhesion to the ZP because of the increased binding avidity produced by multivalent interactions. Oligomerization could also promote membrane protein aggregation that may be important for induction of the sperm acrosome reaction (Leyton & Saling, 1989; Macek et al., 1991).

Other functions of vWF D-domains include heparin and Factor VIII binding (Meyer & Girma, 1993). These vWF D-domain properties have potentially important implications for p105/45 function in sperm physiology. Heparin and/or other glycosaminoglycans promote capacitation and acrosome reaction of bovine spermatozoa in vitro (Parrish et al., 1989), but the target(s) on spermatozoa for these agents is unknown. In addition, a possible requirement for sperm surface proteolytic activity in sperm adhesion to the ZP has been reported (Saling, 1981). By analogy to vWF, it is possible that binding of heparin and/or a protease to the D-domains of p105/45 affect sperm physiology. For example, action of a specific processing protease that binds to a p105/45 D-domain may be necessary for activation of p105/45 during capacitation. Such specific hypotheses can now be tested with recombinant p105/45 expressed in heterologous cells.

Northern blots of poly(A)⁺RNAs from several pig tissues detected expression of p105/45 message only in testis, and within the testis, expression was restricted to the germinal epithelium of the seminiferous tubules, specifically spermatids. Only a fraction of the tubules in a given tissue section appeared to be expressing p105/45 message, consistent with the asynchrony of spermiogenesis among tubules. Spermatid-specific expression of the p105/45 message is consistent with participation of this protein in sperm adhesion to the ZP, since this is a sperm-specific function.

REFERENCES

The following references, to the extent that they provide exemplary procedural or other details supplementary to those set forth herein, are specifically incorporated herein by reference.

Baba et al., *J. Biol. Chem.*, 264:11920–11927, 1989.
Bleil & Wassarman, *J. Cell Biol.*, 102:1363–1371, 1986.
Bleil & Wassarman, *Proc. Natl. Acad. Sci. USA*, 87:5563–5567, 1990.
Cherr et al., *Dev. Biol.*, 114:119–131, 1986.
Chomczynski & Sacchi, "Single-step method of RNA isolation by acid guanidinium thiocyanate-phenol-chloroform extraction," *Anal. Biochem.*, 162:156–159, 1987.
Dunbar et al., *Biochemistry*, 2:356–265, 1980.
Fernandez et al., *Anal. Biochem.*, 201:255–264, 1992.
Florman & First, *Dev. Biol.*, 128:453–463, 1988.
Florman et al., *Dev. Biol.*, 135:133–146, 1989.
Gillis et al., *Prep. Biochem.*, 8:363–378, 1978.
Hardy & Garbers, *Molecular Biology of the Male Reproductive System*, 233–270, 1993.
Hardy et al., *Biol. Reprod.*, 37:189–199, 1987.
Hedrick & Hardy, *Methods Cell Biol.*, 36:231–247, 1991.
Hilkens et al., "Cell membrane-associated mucins and their adhesion-modulating property," *Trends Biochem. Sci.*, 17:359–363, 1992.
Jonakova et al., *FEBS Lett.*, 280:183–186, 1991.
Jones & Brown, *Exp. Cell Res.*, 171:503–508, 1987.
Kinloch et al., *Dev. Biol.*, 142:414–421, 1990.
Kozac, "The scanning model for translation: an update," *J. Cell. Biol.*, 108:229–241, 1989.
Krupinski et al., *Science*, 244:1558–1564, 1989.
Laemmli, *Nature*, 227:680–685, 1970.
Leyton & Saling, "Evidence that aggregation of mouse sperm receptors by ZP3 triggers the acrosome reaction," *J. Cell. Biol.*, 108:2163–2168, 1989.
Leyton & Saling, *Cell*, 57:1123–1130, 1989.
Lopez et al., *J. Biol. Chem.*, 266:15984–15991, 1991.
Macek et al., "Aggregation of β-1,4-galactosyltransferase on mouse sperm induces the acrosome reaction," *Dev. Biol.* 147:440–444, 1991.
Mayadas & Wagner, "Vicinal cysteines in the prosequence play a role in von Willeband factor multimer assembly," *Proc. Natl. Acad. Sci. USA*, 89:3531–3535, 1992.
Meyer & Girma, "von Willebrand factor: structure and function," *Thrombosis Haemostasis*, 70:99–104, 1993.
Miller et al., *Nature*, 357:589–593, 1992.
Moller et al., *Dev. Biol.*, 137:276–286, 1990.
O'Rand et al., *J. Exp. Zool.*, 235:423–428, 1985.
Parrish et al., "Effect of sulfated glycoconjugates on capacitation and the acrosome reaction of bovine and hamster sperm," *Gamete Res.*, 24:403–413, 1989.
Parry et al., *Mol. Reprod. Devel.*, 33:108–115, 1992.
Peterson et al., *Science*, 207:73–74, 1980.
Primakoff et al., *J. Cell Biol.*, 101:2239–2244, 1985
Primakoff et al., *Biol. Reprod.*, 38:921–934, 1988.
Sacco et al., *Biol. Reprod.*, 41:523–532, 1989.
Saling, "Involvement of trypsin-like activity in binding of mouse spermatozoa to zonae pellucida," *Proc. Natl. Acad. Sci. USA*, 78:6231–6235, 1981.
Sambrook et al., "Molecular Cloning: A Laboratory Manual," Cold Spring Harbor Laboratory Press, Second Edition, 1989.
Sanger et al., "DNA sequencing with chain-terminating inhibitors," *Proc. Natl. Acad. Sci. USA*, 74:5463, 1977.
Schmell & Gulyas, *Biol. Reprod.*, 23:1075–1085, 1980.
Shur, *Biochim. Biophys. Acta*, 988:389–409, 1989.
Shur & Neely, *J. Biol. Chem.*, 263:17706–17714, 1988.
Smith et al., *Anal. Biochem.*, 150:76–85, 1985.
Topfer-Peterson & Henschen, *FEBS Lett.*, 226:38–42, 1987,
Towbin et al., *Proc. Natl. Acad. Sci. USA*, 76:4350–4354, 1979.
Urch & Patel, *Development*, 111:1165–1172, 1991.
Uto et al., *J. Exp. Zool.*, 248:113–120, 1988.
Vassar et al., "Spatial segregation of odorant receptor expression in the mammalian olfactory epithelium," *Cell*, 74:309–318, 1993.
Ward & Kopf, *Dev. Biol.*, 158:9–34, 1993.
Wassarman, *Annu. Rev. Biochem.*, 57:415–442, 1988.
Williams & Jones, *J. Exp. Zool.*, 266:65–73, 1993.
Yanagimachi, *Fertilization and Embryonic Development In Vitro*, 81–182, 1981.
Yurewicz et al., *Biochim Biophys. Acta*, 1174:211–214, 1993.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the composition, methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

What is claimed is:

1. A DNA segment comprising an isolated gene that encodes a mammalian egg-binding protein or peptide that comprises the amino acid sequence of SEQ ID NO:2.

2. The DNA segment of claim 1 that comprises a gene that encodes a protein of about 2476 amino acids in length.

3. A DNA segment that comprises a nucleic acid sequence of SEQ ID NO:1.

4. The DNA segment of claim 1, wherein said DNA is operatively linked to a promoter, said promoter expressing the DNA segment.

5. The DNA segment of claim 1, further defined as a recombinant vector.

6. A nucleic acid segment that comprises at least a 14 nucleotide long contiguous stretch that corresponds to a nucleic acid sequence of SEQ ID NO:1.

7. A DNA segment, comprising a contiguous nucleic acid sequence from between position 298 and position 7428 of SEQ ID NO:1.

8. A DNA segment, comprising a nucleic acid sequence encoding the amino acid sequence of SEQ ID NO:5, SEQ ID NO:6, SEQ ID NO:7 or SEQ ID NO:8.

9. A DNA segment, comprising the nucleic acid sequence of SEQ ID NO:3 or SEQ ID NO:4.

10. A recombinant host cell comprising the DNA segment of claim 1.

11. An isolated nucleic acid segment characterized as:

(a) a nucleic acid segment comprising a sequence region that consists of at least 14 contiguous nucleotides that have the same sequence as, or are complementary to, 14 contiguous nucleotides of SEQ ID NO:1; or (b) a nucleic acid segment of from 14 to 7785 nucleotides in length that hybridizes to the nucleic acid segment of SEQ ID NO:1, or the complement thereof, under high stringency hybridization conditions.

12. The nucleic acid segment of claim 11, wherein the segment comprises a sequence region of about 7785 nucleotides; or wherein the segment is about 7785 nucleotides in length.

13. The nucleic acid segment of claim 11, further defined as an RNA segment.

14. The nucleic acid segment of claim 11 further defined as encoding the amino acid sequence of SEQ ID NO:2.

15. The nucleic acid segment of claim 11, further defined as a encoding the amino acid sequence of SEQ ID NO:5, SEQ ID NO:6, SEQ ID NO:7, or SEQ ID NO:8.

16. A method of using the DNA segment of SEQ ID NO:1 comprising the steps of:
 a) preparing a recombinant vector in which the DNA segment comprising SEQ ID NO:1 is positioned under the control of a promoter;
 b) introducing said recombinant vector into a host cell;
 c) culturing the host cell under conditions effective to allow expression of said encoded protein or peptide; and
 d) collecting the protein or peptide expressed.

17. The method of claim 16, wherein said DNA segment comprises a nucleic acid segment encoding the amino acid sequence of SEQ ID NO:2.

18. The method of claim 16, wherein said DNA segment comprises a nucleic acid segment encoding the amino acid sequence of SEQ ID NO:5, SEQ ID NO:6, SEQ ID NO:7 or SEQ ID NO:8.

19. The method of claim 16, wherein said DNA segment comprises the nucleic acid sequence of SEQ ID NO:3 or SEQ ID NO:4.

* * * * *